United States Patent
Montclare et al.

(10) Patent No.: US 10,463,752 B2
(45) Date of Patent: Nov. 5, 2019

(54) PROTEIN POLYMER GOLD NANOPARTICLE HYBRID MATERIALS FOR SMALL MOLECULE DELIVERY

(71) Applicant: New York University, New York, NY (US)

(72) Inventors: Jin Kim Montclare, New York, NY (US); Joseph Frezzo, Brooklyn, NY (US); Min Dai, New York, NY (US); Raymond Chen, Whitestone, NY (US)

(73) Assignee: New York University, New York, NY (US)

( * ) Notice: Subject to any disclaimer, the term of this patent is extended or adjusted under 35 U.S.C. 154(b) by 229 days.

(21) Appl. No.: 15/400,342

(22) Filed: Jan. 6, 2017

(65) Prior Publication Data

US 2017/0196984 A1 Jul. 13, 2017

Related U.S. Application Data

(60) Provisional application No. 62/275,977, filed on Jan. 7, 2016.

(51) Int. Cl.
*A61K 49/18* (2006.01)
(52) U.S. Cl.
CPC .................. *A61K 49/1878* (2013.01)
(58) Field of Classification Search
None
See application file for complete search history.

(56) References Cited

PUBLICATIONS

Rastogi et al., "Highly stable, protein capped gold nanoparticles as effective drug delivery vehicles for amino-glycosidic antibiotics", Materials Science and Engineering C 32: 1571-1577 (2012) (Year: 2012).*

Lin et al., "Genetically Programmable Thermoresponsive Plasmonic Gold/Silk Elastin Protein Core/Shell Nanoparticles", Langmuir 30: 4406-4414 (2014) (Year: 2014).*

Surujpaul, P.P., et al., Gold nanoparticles conjugated to [Tyr3]Octreotide peptide, Biophysical Chemistry, Dec. 2008, vol. 138, No. 3, pp. 83-90.

Sershen, S.R., et al., Temperature-sensitive polymer-nanoshell composites for photothermally modulated drug delivery, Journal of Biomedical Materials Research, Jun. 28, 2000, vol. 51, No. 3, pp. 293-298.

Mathiyazhakan, M., et al., Non-invasive controlled release from gold nanoparticle integrated photo-responsive liposomes through pulse laser induced microbubble cavitation, Colloids and Surfaces B: Biointerfaces, Feb. 2015, vol. 126, pp. 569-574.

De, M., et al., Sensing of proteins in human serum using conjugates of nanoparticles and green fluorescent protein, Nature Chemistry, Aug. 24, 2009, vol. 1, No. 6, pp. 461-465.

Stevens, M.M., et al., Coiled-Coil Peptide-Based Assembly of Gold Nanoparticles, Advanced Materials, Apr. 20, 2004, vol. 16, No. 11, pp. 915-918.

* cited by examiner

*Primary Examiner* — Anand U Desai
(74) *Attorney, Agent, or Firm* — Hodgson Russ LLP

(57) ABSTRACT

Protein polymer-gold nanoparticles, compositions comprising protein polymer-gold nanoparticles, and uses of protein polymer-gold nanoparticles. A protein polymer-gold nanoparticle comprises a gold core and a plurality of protein polymer molecules coordinated to the gold core via a poly-histidine tag present on each protein polymer molecule. A protein polymer molecule comprises one or more elastin-like polypeptide domain and a coiled-coil region of Cartilage Oligomeric Matrix Protein domain or a variant thereof. For example, the protein polymer-gold nanoparticles can be used in methods of small molecule delivery to an individual.

26 Claims, 11 Drawing Sheets

Specification includes a Sequence Listing.

A.

CE₁-His₆    MRGSHHHHHHGSACELAATATATATATAACGDLAPQMLRELQETNAALQDVRELLRQQVKEITFLKNTVMESDAS
            GLQAATATATATATAVPGVGVPGFGVPGVGVPGVGVPGVGVPLEGSGTGAKLN

CE₁-IEGR    MRGSHHHHHHIEGRELAATATATATATAACGDLAPQMLRELQETNAALQDVRELLRQQVKEITFLKNTVMESDAS
            GLQAATATATATATAVDKPIAASAVPGVGVPGFGVPGVGVPGVGVPGVGVPLEGSGTGAKLN

E₁C-His₆    MRGSHHHHHHGSKPIAASAVPGVGVPGVGVPGFGVPGVGVPGVGVPLEGSELAATATATATATAACGDLAPQML
            RELQETNAALQDVRELLRQQVKEITFLKNTVMESDASGLQAATATATATATAVDLQPS

E₁C-IEGR    MRGSHHHHHHIEGRIAASAVPGVGVPGVGVPGFGVPGVGVPGVGVPLEGSELAATATATATATAACGDLAPQML
            RELQETNAALQDVRELLRQQVKEITFLKNTVMESDASGLQAATATATATATAVDLQPS

SEQUENCE LISTING

```
<160> NUMBER OF SEQ ID NOS: 32

<210> SEQ ID NO 1
<211> LENGTH: 46
<212> TYPE: PRT
<213> ORGANISM: Artificial Sequence
<220> FEATURE:
<223> OTHER INFORMATION: Synthetic Protein

<400> SEQUENCE: 1

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Cys Asp Ala Cys Gly
        35                  40                  45

<210> SEQ ID NO 2
<211> LENGTH: 46
<212> TYPE: PRT
<213> ORGANISM: Artificial Sequence
<220> FEATURE:
<223> OTHER INFORMATION: Synthetic Protein

<400> SEQUENCE: 2

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 3
<211> LENGTH: 46
<212> TYPE: PRT
<213> ORGANISM: Artificial Sequence
<220> FEATURE:
<223> OTHER INFORMATION: Synthetic Protein

<400> SEQUENCE: 3

Gly Asp Leu Ala Pro Gln Met Leu Arg Glu Ala Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45
```

-continued

<210> SEQ ID NO 4
<211> LENGTH: 46
<212> TYPE: PRT
<213> ORGANISM: Artificial Sequence
<220> FEATURE:
<223> OTHER INFORMATION: Synthetic Protein

<400> SEQUENCE: 4

Gly Asp Leu Ala Pro Gln Met Leu Arg Glu Leu Gln Glu Ala Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 5
<211> LENGTH: 46
<212> TYPE: PRT
<213> ORGANISM: Artificial Sequence
<220> FEATURE:
<223> OTHER INFORMATION: Synthetic Protein

<400> SEQUENCE: 5

Gly Asp Leu Ala Pro Gln Met Leu Arg Glu Leu Gln Glu Thr Asn Ala
1               5                   10                  15

Ala Ala Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 6
<211> LENGTH: 46
<212> TYPE: PRT
<213> ORGANISM: Artificial Sequence
<220> FEATURE:
<223> OTHER INFORMATION: Synthetic Protein

<400> SEQUENCE: 6

Gly Asp Leu Ala Pro Gln Met Leu Arg Glu Leu Gln Glu Thr Asn Ala
1               5                   10                  15

Ala Leu Gln Asp Ala Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 7
<211> LENGTH: 46
<212> TYPE: PRT
<213> ORGANISM: Artificial Sequence
<220> FEATURE:
<223> OTHER INFORMATION: Synthetic Protein

<400> SEQUENCE: 7

Gly Asp Leu Ala Pro Gln Met Leu Arg Glu Leu Gln Glu Thr Asn Ala
1               5                   10                  15

Ala Leu Gln Asp Val Arg Glu Leu Ala Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 8
<211> LENGTH: 46

<212> TYPE: PRT
<213> ORGANISM: Artificial Sequence
<220> FEATURE:
<223> OTHER INFORMATION: Synthetic Protein

<400> SEQUENCE: 8

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Ala Val Lys Glu Ile
            20                  25                  30

Thr Phe Leu Lys Asn Thr Val Met Glu Ser Asp Ala Ser Gly
        35                  40                  45

<210> SEQ ID NO 9
<211> LENGTH: 46
<212> TYPE: PRT
<213> ORGANISM: Artificial Sequence
<220> FEATURE:
<223> OTHER INFORMATION: Synthetic Protein

<400> SEQUENCE: 9

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ala
            20                  25                  30

Thr Phe Leu Lys Asn Thr Val Met Glu Ser Asp Ala Ser Gly
        35                  40                  45

<210> SEQ ID NO 10
<211> LENGTH: 46
<212> TYPE: PRT
<213> ORGANISM: Artificial Sequence
<220> FEATURE:
<223> OTHER INFORMATION: Synthetic Protein

<400> SEQUENCE: 10

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Ala Lys Asn Thr Val Met Glu Ser Asp Ala Ser Gly
        35                  40                  45

<210> SEQ ID NO 11
<211> LENGTH: 46
<212> TYPE: PRT
<213> ORGANISM: Artificial Sequence
<220> FEATURE:
<223> OTHER INFORMATION: Synthetic Protein

<400> SEQUENCE: 11

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Ala Met Glu Ser Asp Ala Ser Gly
        35                  40                  45

<210> SEQ ID NO 12
<211> LENGTH: 46
<212> TYPE: PRT
<213> ORGANISM: Artificial Sequence
<220> FEATURE:

<223> OTHER INFORMATION: Synthetic Protein

<400> SEQUENCE: 12

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ala Asp Ala Ser Gly
        35                  40                  45

<210> SEQ ID NO 13
<211> LENGTH: 141
<212> TYPE: PRT
<213> ORGANISM: Artificial Sequence
<220> FEATURE:
<223> OTHER INFORMATION: Synthetic Protein

<400> SEQUENCE: 13

Met Arg Gly Ser His His His His His His Gly Ser Ala Cys Glu Leu
1               5                   10                  15

Ala Ala Thr Ala Thr Ala Thr Ala Thr Ala Thr Ala Thr Ala Ala Cys
            20                  25                  30

Gly Asp Leu Ala Pro Gln Met Leu Arg Glu Leu Gln Glu Thr Asn Ala
        35                  40                  45

Ala Leu Gln Asp Val Arg Glu Leu Leu Arg Gln Gln Val Lys Glu Ile
    50                  55                  60

Thr Phe Leu Lys Asn Thr Val Met Glu Ser Asp Ala Ser Gly Leu Gln
65                  70                  75                  80

Ala Ala Thr Ala Thr Ala Thr Ala Thr Ala Thr Ala Thr Ala Val Asp
                85                  90                  95

Lys Pro Ile Ala Ala Ser Ala Val Pro Gly Val Gly Val Pro Gly Val
            100                 105                 110

Gly Val Pro Gly Phe Gly Val Pro Gly Val Gly Val Pro Gly Val Gly
        115                 120                 125

Val Pro Leu Glu Gly Ser Gly Thr Gly Ala Lys Leu Asn
    130                 135                 140

<210> SEQ ID NO 14
<211> LENGTH: 136
<212> TYPE: PRT
<213> ORGANISM: Artificial Sequence
<220> FEATURE:
<223> OTHER INFORMATION: Synthetic Protein

<400> SEQUENCE: 14

Met Arg Gly Ser His His His His His His Gly Ser Lys Pro Ile Ala
1               5                   10                  15

Ala Ser Ala Val Pro Gly Val Gly Val Pro Gly Val Gly Val Pro Gly
            20                  25                  30

Phe Gly Val Pro Gly Val Gly Val Pro Gly Val Gly Val Pro Leu Glu
        35                  40                  45

Gly Ser Glu Leu Ala Ala Thr Ala Thr Ala Thr Ala Thr Ala Thr Ala
    50                  55                  60

Thr Ala Ala Cys Gly Asp Leu Ala Pro Gln Met Leu Arg Glu Leu Gln
65                  70                  75                  80

Glu Thr Asn Ala Ala Leu Gln Asp Val Arg Glu Leu Leu Arg Gln Gln
                85                  90                  95

Val Lys Glu Ile Thr Phe Leu Lys Asn Thr Val Met Glu Ser Asp Ala

```
              100                 105                 110
Ser Gly Leu Gln Ala Ala Thr Ala Thr Ala Thr Ala Thr Ala
        115                 120                 125

Thr Ala Val Asp Leu Gln Pro Ser
        130                 135

<210> SEQ ID NO 15
<211> LENGTH: 46
<212> TYPE: PRT
<213> ORGANISM: Artificial Sequence
<220> FEATURE:
<223> OTHER INFORMATION: Synthetic Protein

<400> SEQUENCE: 15

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Ser Asp Ala Ser Gly
        35                  40                  45

<210> SEQ ID NO 16
<211> LENGTH: 25
<212> TYPE: PRT
<213> ORGANISM: Artificial Sequence
<220> FEATURE:
<223> OTHER INFORMATION: Synthetic Protein

<400> SEQUENCE: 16

Val Pro Gly Val Gly Val Pro Gly Val Gly Val Pro Gly Phe Gly Val
1               5                   10                  15

Pro Gly Val Gly Val Pro Gly Val Gly
            20                  25

<210> SEQ ID NO 17
<211> LENGTH: 4
<212> TYPE: PRT
<213> ORGANISM: Artificial Sequence
<220> FEATURE:
<223> OTHER INFORMATION: Synthetic Protein

<400> SEQUENCE: 17

Ile Glu Gly Arg
1

<210> SEQ ID NO 18
<211> LENGTH: 141
<212> TYPE: PRT
<213> ORGANISM: Artificial Sequence
<220> FEATURE:
<223> OTHER INFORMATION: Synthetic Protein

<400> SEQUENCE: 18

Met Arg Gly Ser His His His His His His Ile Glu Gly Arg Glu Leu
1               5                   10                  15

Ala Ala Thr Ala Thr Ala Thr Ala Thr Ala Thr Ala Thr Ala Ala Cys
            20                  25                  30

Gly Asp Leu Ala Pro Gln Met Leu Arg Glu Leu Gln Glu Thr Asn Ala
        35                  40                  45

Ala Leu Gln Asp Val Arg Glu Leu Leu Arg Gln Gln Val Lys Glu Ile
    50                  55                  60

Thr Phe Leu Lys Asn Thr Val Met Glu Ser Asp Ala Ser Gly Leu Gln
```

```
                65                  70                  75                  80
Ala Ala Thr Ala Thr Ala Thr Ala Thr Ala Thr Ala Val Asp
                    85                  90                  95
Lys Pro Ile Ala Ala Ser Ala Val Pro Gly Val Gly Val Pro Gly Val
                100                 105                 110
Gly Val Pro Gly Phe Gly Val Pro Gly Val Gly Val Pro Gly Val Gly
                115                 120                 125
Val Pro Leu Glu Gly Ser Gly Thr Gly Ala Lys Leu Asn
    130                 135                 140
```

<210> SEQ ID NO 19
<211> LENGTH: 136
<212> TYPE: PRT
<213> ORGANISM: Artificial Sequence
<220> FEATURE:
<223> OTHER INFORMATION: Synthetic Protein

<400> SEQUENCE: 19

```
Met Arg Gly Ser His His His His His His Ile Glu Gly Arg Ile Ala
1               5                   10                  15
Ala Ser Ala Val Pro Gly Val Gly Val Pro Gly Val Gly Val Pro Gly
                20                  25                  30
Phe Gly Val Pro Gly Val Gly Val Pro Gly Val Gly Val Pro Leu Glu
                35                  40                  45
Gly Ser Glu Leu Ala Ala Thr Ala Thr Ala Thr Ala Thr Ala Thr Ala
            50                  55                  60
Thr Ala Ala Cys Gly Asp Leu Ala Pro Gln Met Leu Arg Glu Leu Gln
65                  70                  75                  80
Glu Thr Asn Ala Ala Leu Gln Asp Val Arg Glu Leu Leu Arg Gln Gln
                85                  90                  95
Val Lys Glu Ile Thr Phe Leu Lys Asn Thr Val Met Glu Ser Asp Ala
                100                 105                 110
Ser Gly Leu Gln Ala Ala Thr Ala Thr Ala Thr Ala Thr Ala Thr Ala
            115                 120                 125
Thr Ala Val Asp Leu Gln Pro Ser
    130                 135
```

<210> SEQ ID NO 20
<211> LENGTH: 14
<212> TYPE: PRT
<213> ORGANISM: Artificial Sequence
<220> FEATURE:
<223> OTHER INFORMATION: Synthetic Protein

<400> SEQUENCE: 20

```
Met Arg Gly Ser His His His His His His Ile Glu Gly Arg
1               5                   10
```

<210> SEQ ID NO 21
<211> LENGTH: 14
<212> TYPE: PRT
<213> ORGANISM: Artificial Sequence
<220> FEATURE:
<223> OTHER INFORMATION: Synthetic Protein

<400> SEQUENCE: 21

```
Met Arg Gly Ser His His His His His His Gly Ser Ala Cys
1               5                   10
```

<210> SEQ ID NO 22

```
<211> LENGTH: 14
<212> TYPE: PRT
<213> ORGANISM: Artificial Sequence
<220> FEATURE:
<223> OTHER INFORMATION: Synthetic Protein

<400> SEQUENCE: 22

Met Arg Gly Ser His His His His His His Gly Ser Lys Pro
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Synthetic Protein

<400> SEQUENCE: 23

Ile Ala Ala Ser Ala
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic Protein

<400> SEQUENCE: 24

Ala Thr Ala Thr Ala Thr Ala Thr Ala Thr Ala Thr
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Protein

<400> SEQUENCE: 25

Leu Glu Gly Ser Glu Leu Ala
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic Protein

<400> SEQUENCE: 26

Ala Val Asp Lys Pro Ile Ala Ala Ser Ala
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic Protein

<400> SEQUENCE: 27

Leu Glu Gly Ser Gly Thr Gly Ala Lys Leu Asn
1               5                   10

<210> SEQ ID NO 28
<211> LENGTH: 7
```

<212> TYPE: PRT
<213> ORGANISM: Artificial Sequence
<220> FEATURE:
<223> OTHER INFORMATION: Synthetic Protein

<400> SEQUENCE: 28

Ala Val Asp Leu Gln Pro Ser
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic Protein
<220> FEATURE:
<221> NAME/KEY: MISC_FEATURE
<222> LOCATION: (4)..(4)
<223> OTHER INFORMATION: Xaa can be any amino acid except proline

<400> SEQUENCE: 29

Val Pro Gly Xaa Gly
1               5

<210> SEQ ID NO 30
<211> LENGTH: 25
<212> TYPE: PRT
<213> ORGANISM: Artificial Sequence
<220> FEATURE:
<223> OTHER INFORMATION: Synthetic Protein
<220> FEATURE:
<221> NAME/KEY: MISC_FEATURE
<222> LOCATION: (4)..(4)
<223> OTHER INFORMATION: Xaa can be any amino acid except proline.
<220> FEATURE:
<221> NAME/KEY: MISC_FEATURE
<222> LOCATION: (9)..(9)
<223> OTHER INFORMATION: Xaa can be any amino acid except proline.
<220> FEATURE:
<221> NAME/KEY: MISC_FEATURE
<222> LOCATION: (14)..(14)
<223> OTHER INFORMATION: Xaa can be any amino acid except proline.
<220> FEATURE:
<221> NAME/KEY: MISC_FEATURE
<222> LOCATION: (19)..(19)
<223> OTHER INFORMATION: Xaa can be any amino acid except proline.
<220> FEATURE:
<221> NAME/KEY: MISC_FEATURE
<222> LOCATION: (24)..(24)
<223> OTHER INFORMATION: Xaa can be any amino acid except proline.

<400> SEQUENCE: 30

Val Pro Gly Xaa Gly Val Pro Gly Xaa Gly Val Pro Gly Xaa Gly Val
1               5                   10                  15

Pro Gly Xaa Gly Val Pro Gly Xaa Gly
            20                  25

<210> SEQ ID NO 31
<211> LENGTH: 45
<212> TYPE: DNA
<213> ORGANISM: Artificial Sequence
<220> FEATURE:
<223> OTHER INFORMATION: Synthetic Protein

<400> SEQUENCE: 31
cgcagtagca gcgagctcgc gcccttctat gtgatggtga tggtg                    45

<210> SEQ ID NO 32
<211> LENGTH: 42
<212> TYPE: DNA

```
<213> ORGANISM: Artificial Sequence
<220> FEATURE:
<223> OTHER INFORMATION: Synthetic Protein

<400> SEQUENCE: 32
cgcgctagcc gcaatgcgcc cttctatgtg atggtgatgg tg                          42
```

PROTEIN POLYMER GOLD NANOPARTICLE HYBRID MATERIALS FOR SMALL MOLECULE DELIVERY

CROSS REFERENCE TO RELATED APPLICATIONS

This application claims priority to U.S. Provisional Application No. 62/275,977 filed on Jan. 7, 2016, the disclosure of which is incorporated herein by reference.

STATEMENT REGARDING FEDERALLY SPONSORED RESEARCH

This invention was made with government support under contract nos. DMR-1205384 and DMR-1420073 awarded by the National Science Foundation. The government has certain rights in the invention.

BACKGROUND OF THE DISCLOSURE

Controlled release and efficient loading continue to be challenges in the area of drug delivery vehicles. Composite hydrogel material comprised of temperature-sensitive copolymers, N-isopropylacrylamide and acrylamide, embedded with gold nanoparticles (GNPs,) bearing a gold sulfide nanoshell designed to absorb and convert near-IR light to heat are known for drug release (Sershen et al., *Journal of Biomedical Materials Research* 2000, 51, (3), 293-298). Another example of using gold nanoparticles for triggered drug release relies on liposomal nanoparticles composed 1,2-dipalmitoyl-sn-glycero-3-phosphocholine, 1-palmitoyl-2-hydroxy-sn-glycero-3-phosphocholine and 1,2-distearoyl-sn-glycero-3-phosphoethanol-amine-N-[carboxy(polyethylene glycol)-2000]. Such liposomes, when loaded with both GNPs and the hydrophilic drug calcein, leads to light controlled calcein release due to microbubble cavitation of the liposome membrane upon treatment with 532 nm (Mathiyazhakan et al., *Colloids and Surfaces B: Biointerfaces* 2015, 126, 569-574). Synthetic materials have been developed and explored, proteins have attracted attention due to the fine molecular and conformational control of sequence and structure. Recently, GNPs have been decorated with a library of cationic groups that complex non-covalently with green fluorescent protein (GFP) (De et al., *Nat Chem* 2009, 1, (6), 461-465). These GFP•GNP complexes have been employed in an array to chemically detect human serum proteins in complex serum. In this case, the strategy for construction of such protein•GNP hybrids rely on the covalent or non-covalent linkage of chemically pre-fabricated GNPs (Stevens et al., *Advanced Materials* 2004, 16, (11), 915-918; Slocik et al., *Nano Letters* 2002, 2, (3), 169-173); such GNPs are synthesized under bio-incompatible and harsh conditions including high temperatures, organic solvents and need of external capping agents.

SUMMARY OF THE DISCLOSURE

In this disclosure, we provide multifunctional protein materials capable of one or more of: (i) templated-synthesis of inorganic nanoparticles in situ to fabricate organic-inorganic hybrids without the need for covalent bonding between each substituent part; (ii) incorporating and stabilizing large payloads of small molecules; and (iii) modulating the delivery of small molecule chemotherapeutic drugs in clinically relevant cells. For example, provided herein is a drug delivery system that can solubilize and stabilize labile molecules for therapeutic applications.

We have fabricated protein polymer•gold nanoparticles (P•G nanoparticles or P•G NPs), also referred to herein as nanocomposites, that exhibit enhanced binding and delivery of small hydrophobic molecules. For example, P•G NPs exhibit enhanced binding a delivery of curcumin to a model breast cancer cell line, MCF-7. The P•G NPs can be constructed via in situ G core templated-synthesis with genetically engineered histidine tags. The P•G NPs exhibit enhanced small molecule loading and sustained release and increased uptake by cells. When compared to the proteins polymers alone, the P•G NPs demonstrated a greater than 7-fold increase in curcumin binding, a nearly 50% slower release profile and more than 2-fold increase in cellular uptake of curcumin. The P•G NPs can serve as drug delivery vehicles.

In an aspect, the present disclosure provides a protein polymer-gold nanoparticle, where the gold forms the core of the nanoparticle and a plurality of protein polymer molecules are coordinated to the gold core via poly-histidine tag present on each protein polymer molecule, wherein the protein polymer molecule comprises one or more elastin-like polypeptide domain (E) and a coiled-coil region of Cartilage Oligomeric Matrix Protein domain (C) or a variant thereof. In an example, the average size of the gold core is about 2 to 5 nm. In an example, the average size of the nanoparticle is about 18 to 30 nm. In an example, the protein polymer has the structure $CE_x$-$His_y$, or $E_xC$-$His_y$, where x is 1-5, and y is 1-10. In an example, the nanoparticle further comprises one or more types of small molecules. In an example, the small molecules are hydrophobic small molecules and/or hydrophilic small molecules.

In an aspect, the present disclosure provides a composition comprising a protein polymer-gold nanoparticle of the present disclosure (or a plurality of protein polymer-gold nanoparticles of the present disclosure). In an example, the composition comprises one or more pharmaceutical carrier.

In an aspect, the present disclosure provides a composition comprising protein polymer-gold nanoparticles made by a process comprising: a) admixing a composition comprising one or more gold precursor with a composition comprising one or more protein polymer precursor; and b) adding one or more reducing agent to a) for a time sufficient to form the protein polymer-gold nanoparticles (e.g., adding one or more reducing agent to the mixture formed in a), where the protein polymer-gold nanoparticles are formed). In an example, the method further comprises incubating the protein polymer-gold nanoparticles with a composition comprising hydrophobic and/or hydrophilic small molecules thereby incorporating the small molecules in the protein polymer-gold nanoparticles.

In an aspect, the present disclosure provides a method for delivery of hydrophobic small molecules to a target comprising: administering to an individual a composition comprising protein polymer-gold nanoparticles having incorporated therein hydrophobic small molecules such that the nanoparticles are taken up by target cells and the small molecules are released within the target cells. In an example, the method further comprises monitoring the location of the nanoparticles in the individual following administration by magnetic resonance imaging (MRI) of gold. In an example, the method further comprises increasing the temperature of the desired site when the nanoparticles reach the desired site, to a temperature sufficient to facilitate hydrophobic small molecule release from the nanoparticles. In various examples, an increase in the temperature of the desired site is achieved by one or more of the following selected from the group consisting of heating pad, high-intensity focused ultrasound, focused light, and fiber optics.

BRIEF DESCRIPTION OF THE FIGURES

FIG. 6 shows (a) alignment of protein sequences translated from DNAs that were verified by DNA sequencing at Eurofins. His tag cleavage site IEGR (SEQ ID NO: 17) is highlighted with underline in $CE_1$-IEGR (SEQ ID NO: 18) and $E_1C$-IEGR (SEQ ID NO: 19). (b) Representative breakdown of protein sequences with corresponding amino acids above each block. The following sequences are present in (b): $His_6$IEGR (IVIRGSHEIHHHHIEGR) (SEQ ID NO: 20), $His_6$GSAC (IVIRGSHEIREIHHGSAC) (SEQ ID NO: 21), $His_6$GSKP (MRGSHHHHHHGSKP) (SEQ ID NO: 22), IAASA (SEQ ID NO: 23) plasmid sequence, AT-rich linker (ATATATATATAT) (SEQ ID NO: 24); LEGSELA (SEQ ID NO: 25) plasmid sequence, AVDKPIAASA (SEQ ID NO: 26) plasmid sequence, LEGSGTGAKLN (SEQ ID NO: 27) plasmid sequence, and AVDLQPS (SEQ ID NO: 28) plasmid sequence.

DESCRIPTION OF THE DISCLOSURE

Figure 1:
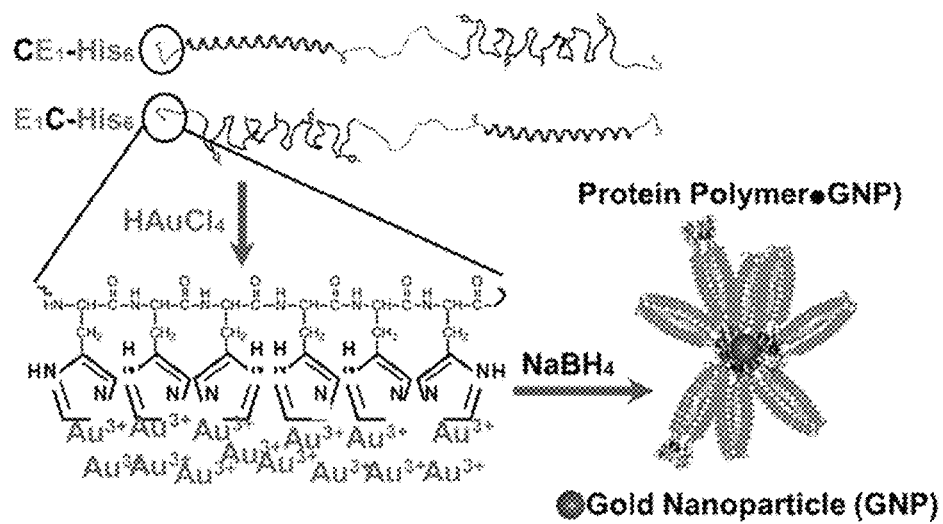
FIG. 1 shows the protein polymer sequences of $CE_1$-$His_6$ (SEQ ID NO: 13) and $E_1C$-$His_6$ (SEQ ID NO: 14) and P•G NP templated-synthesis strategy. Bolded letter "C" indicates a C domain (SEQ ID NO: 15). Faded letter "E" indicates an E domain (SEQ ID NO: 16).

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

By "about" it is meant that a value includes values+/−10% of that value.

This disclosure provides hybrid nanoparticles comprising protein polymer and gold. In this disclosure, the nanoparticles may also be referred to as protein polymer-gold nanoparticles or as polymer-gold nanoparticles. The disclosure also provides methods for making the nanoparticles and methods of using compositions comprising the nanoparticles.

While not intending to be bound by any particular theory, the generated data is consistent with a nanoparticle comprising a gold core, which may be partially or completely surrounded by protein polymer molecules. It is considered that the protein polymers may be coordinated to gold via the N-terminal poly-his tag. The size of the gold core can be from 3 to 4.5 nm (and all sizes and ranges therebetween) and in general, spherical. For example, the average size of the gold core can be about 3.3 to 3.6 nm. The size of the P•G NP can be from about 20 to about 30 nm (and all sizes and ranges therebetween). For example, the average size of the P•G NP can be about 22 to about 28 nm. In various embodiments, at least 80%, 85%, 90%, 95%, or 99% of the particles are within +/−3 nm of the average particle size.

The protein polymer comprises an E domain and a C domain. The E domain refers to elastin-like peptide repeats. Each elastin-like peptide repeat comprises the pentapeptide sequence VPGXG (SEQ ID NO: 29) where the X residue is valine but can be substituted with any amino acid other than proline. It was found that the number of E domain repeats impacted both small molecule binding and the transition temperature. The elastin-like peptide domain can be represented as $E_x$, and the sequence of $E_x$ as [(VPGXG)$_2$VPGXG (VPGXG)$_2$]$_x$, (SEQ ID NO: 30) where x is equal to or greater than 1. For x=1 (represented as $E_1$), the sequence contains 5 VPGXG repeats, and for x=2 (i.e., $E_2$), the sequence contains 10 VPGXG (SEQ ID NO: 29) repeats and so on. x can be from 1 to 24 and all integer values therebetween. Thus, $E_5$ contains 25 VPGXG (SEQ ID NO: 29) repeats and $E_{24}$ contains 120 VPGXG (SEQ ID NO: 29) repeats. The "X" in the repeats can independently at each occurrence be any amino acid other the proline. In one embodiment, X at each occurrence is V. In one embodiment, X at each occurrence can independently be V or F. In some embodiments, from 1-3 amino acids (such as VP) or more may be present at the C-terminus end of the sequence.

The C domain is derived from the N-terminal coiled-coil of cartilage oligomeric matrix protein termed here as COMPcc. The sequences of COMPcc and variants are provided in U.S. Pat. No. 8,790,709, which sequences are incorporated herein by reference. COMPcc can self-assemble into a pentameric alpha helical coiled-coil and also bears a hydrophobic pore (e.g., 7.3 nm long and 0.2-0.6 nm diameter) that is useful for entrapping small molecules such as doxorubicin, vitamin D, all-trans-retinol and curcumin.

Variants of COMPcc (e.g., SEQ ID NOs: 2-12) can be described as having at least 65% homology with SEQ ID NO: 1. In various examples, the variant has at least 70%, at least 75%, at least 80%, at least 85%, at least 90%, or at least 95% homology with SEQ ID NO: 1. In various examples, the variant can have the first six amino acids, first seven amino acids, first eight amino acids, first nine amino acids, or first ten amino acids of SEQ ID NO: 1 unchanged and have at least 65% homology, at least 70%, at least 75%, at least 80%, at least 85%, at least 90%, or at least 95% homology with the remaining sequence.

Any of the COMPcc sequences or variants can be used in the present disclosure. For example, the coiled-coil region of COMP has the following sequence:

```
                                        (SEQ ID NO: 1)
GDLAPQMLRELQETNAALQDVRELLRQQVKEITFLKNTVMECDACG

Some examples of variants of COMPcc are provided
below.
                                        (SEQ ID NO: 2)
GDLAPQMLRELQETNAALQDVRELLRQQVKEITFLKNTVMESDASG (SEQ ID NO: 3)
GDLAPQMLREAQETNAALQDVRELLRQQVKEITFLKNTVMESDASG (SEQ ID NO: 4)
GDLAPQMLRELQEANAALQDVRELLRQQVKEITFLKNTVMESDASG (SEQ ID NO: 5)
GDLAPQMLRELQETNAAAQDVRELLRQQVKEITFLKNTVMESDASG (SEQ ID NO: 6)
GDLAPQMLRELQETNAALQDARELLRQQVKEITFLKNTVMESDASG (SEQ ID NO: 7)
GDLAPQMLRELQETNAALQDVRELARQQVKEITFLKNTVMESDASG (SEQ ID NO: 8)
GDLAPQMLRELQETNAALQDVRELLRQAVKEITFLKNTVMESDASG (SEQ ID NO: 9)
GDLAPQMLRELQETNAALQDVRELLRQQVKEATFLKNTVMESDASG (SEQ ID NO: 10)
GDLAPQMLRELQETNAALQDVRELLRQQVKEITFAKNTVMESDASG (SEQ ID NO: 11)
GDLAPQMLRELQETNAALQDVRELLRQQVKEITFLKNTAMESDASG (SEQ ID NO: 12)
GDLAPQMLRELQETNAALQDVRELLRQQVKEITFLKNTVMEADASG
```

The sequence of the C domain (from the N-terminus) can start with a glycine as shown in the above sequences, or may start at the $2^{nd}$ amino acid, aspartic acid. Thus, this disclosure also provides the use of SEQ ID NOs: 1-12 which do not have an N-terminal glycine.

The protein polymers of the present disclosure comprise a polyhistidine domain, a C domain and an E domain. The polyhistidine domain may be at the N-terminus. For example, in one arrangement, the protein polymer comprises (from N to C terminus): polyhistidine domain, a C domain and an E domain. In another arrangement, the protein polymer may comprise (from N to C terminus): polyhistidine domain, an E domain and a C domain. Additional amino acids may be present at the N or C termini or may be present in between these domains. For example, linkers, AT-rich regions, and/or residual amino acids from cloning process may be present. Some non-restrictive examples are provided below and also illustrated in FIG. 6B.

The protein polymers of the present disclosure may comprise 1) an N-terminal histidine domain connected via a linker to a C domain, which is connected via a second linker to an E domain; or 2) an N-terminal histidine domain connected via a linker to an E domain, which is connected via a second linker to a C domain. The polyhistidine domain comprises a plurality of histidines (six histidines), which can optionally have additional amino acid sequences on the C-terminus and/or N-terminus of the histidine sequence. The linker regions may comprise an amino acid sequence of 8-30 amino acid residues, including all integer number of amino acid residues and ranges therebetween. The linker region may be an AT rich region. Depending upon the arrangement of E and C, the histidine tag may be present on the E or the C. In one example, the number of units of E can be from 1 to 5, including 2, 3, or 4, units of E. For example, the protein polymer can have the structure $CE_x$ or $E_xC$, wherein x is from 1 to 5, including x=2, 3, or 4. Some examples of protein polymers can be seen in FIG. 6. For example, a protein polymer of the present disclosure can comprise an initial N-terminus histidine tag connected to a linker region (e.g., a plasmid sequence connected to an AT-rich linker connected to a second plasmid sequence) connected to a C domain connected to a second linker region (e.g., a plasmid sequence connected to an AT-rich linker connected to a second plasmid sequence) connected to an E domain (with an optional plasmid sequence at the C-terminus). An example of an arrangement of various domains or elements is shown in FIG. 6B. As can be appreciated, unless sequences are specified (such as for the C and E domains and the polyhistidines), the various elements plasmid sequence, linkers may have any amino acid sequence.

The present P•G NPs can be prepared by an in situ method. For example, a gold precursor can be reduced in situ in the presence of the protein polymers thereby providing a templated synthesis of polymer-gold nanoparticles. For example, a gold precursor is reduced in situ to an oxidation state of 0. Any reducing agent can be used to achieve the reduction of the gold precursor. For example, the reducing agent can be sodium borohydride, EDTA, sodium citrate, citric acid, hydroxylamine, acetone, oxalic acid, 4-aminophenol, 3-aminophenol, triethylamine, indoles, 1,4-phenylenediamine, aniline, 4-bromoaniline, 1-methylindole, 3-amino-1-propanol, pyridine, 3-indole propionic acid, glycine, tryptophan and the like and combinations thereof.

Any water soluble gold precursor may be used in the present disclosure. The gold precursor may be monovalent or trivalent. The gold precursor is capable of being reduced in situ to an oxidation state of gold (0). For example, if the gold precursor is trivalent, then it is reduced from gold (III) to gold (0). Suitable gold salts of the present disclosure include, but are not limited to, gold (III) chlorides such as, for example, gold(III) chloride trihydrate and hydrogentetrachloroaurate(III) hydrate. In an embodiment, gold (0) is directly added to the protein polymer.

P•G NPs can be stored at a pH from 7.6 to 9.0 in a suitable buffer for at least up to 2 weeks at refrigeration or room temperatures. Suitable buffers include, but are not limited to, sodium phosphate, sodium bicarbonate, and Tris-HCl. For example, the P•G NPs are stored in sodium phosphate buffer at pH 8.0. In another example, the P•G NPs are stored in sodium bicarbonate buffer at pH 8.5. In yet another example, the P•G NPs are stored in Tris-HCl buffer at pH 8.0.

The P•G NPs can be loaded with delivery molecules, which may be hydrophobic or hydrophilic. The load may comprise a plurality of the same types of molecules or different types of molecules. In one embodiment, the load comprises small hydrophobic molecules. Examples include, but are not limited to, doxorubicin, vitamin D, all-trans-retinol, curcumin, retinoid antagonists/inverse agonists, taxol, steroids, peptides, other anticancer and antiarthritis drugs, and the like. The molar ratio of small molecule to protein polymer can be from 0.4:1 to 4.0:1. For example, the molar ratio can be from 0.4:1 to 4.0:1 and all values therebetween. The ratio may be 0.5:1, 1:1, 1.5:1, 2:1, 2.5:1, 3:1, 3.5:1, or 4:1.

For loading of the cargo, the cargo can be incubated with the P•G NPs at room temperature, in 50 mM sodium phosphate buffer at pH 7.4. If the cargo is a fluorescent or light sensitive molecule, the incubation can be carried out in dark for a suitable period of time (such as, for example, two hours).

The proteins of the present disclosure include functionally equivalent molecules in which amino acid residues are substituted for residues within the sequence resulting in a silent or conservative change. For example, one or more amino acid residues within the sequence can be substituted by another amino acid of a similar polarity that acts as a functional equivalent, resulting in a silent or conservative alteration. Substitutes for an amino acid within the sequence may be selected from other members of the class to which the amino acid belongs. For example, the nonpolar (hydrophobic) amino acids include, but are not limited to, alanine, leucine, isoleucine, valine, proline, phenylalanine, tryptophan, methionine, and combinations thereof. The polar neutral amino acids include, but are not limited to, glycine, serine, threonine, cysteine, tyrosine, asparagine and glutamine, and combinations thereof. The positively charged (basic) amino acids include, but are not limited to, arginine, lysine and histidine. The negatively charged (acidic) amino acids include aspartic acid, glutamic acid, and combinations thereof. In one embodiment, one or more cysteine moieties are replaced with serine moieties. Also included within the scope of the disclosure are proteins or fragments or derivatives thereof which exhibit the same or similar biological activity and derivatives which are differentially modified during or after translation, for example, by glycosylation, proteolytic cleavage, and linkage to other ligands.

The present disclosure provides P•G NPs made by forming a reaction mixture comprising one or more gold precursor, one or more protein polymer precursor, and one or more reducing agent, where P•G NPs of the present disclosure are formed. For example, a method of making P•G NPs of the present disclosure comprises a) adding a solution comprising gold precursor to a solution comprising the protein polymer precursor; and b) adding a reducing agent to the solution of a) for a time sufficient to form the P•G NPs. The nanoparticles have enhanced drug loading and sustained drug release characteristics compared to protein polymer delivery systems that do not have a gold core.

The present disclosure also provides a method for delivery of small molecules (such as, for example, hydrophobic small molecules) to a target comprising administering to a patient a composition comprising P•G NPs into which are incorporated one or more small molecules or one or more types of small molecules. In an embodiment, the method may further comprise increasing the temperature of the desired target site to a temperature sufficient to facilitate hydrophobic small molecule release. The temperature of the target site may be increased when the nanoparticles reach the site or prior to that. The temperature of a desired target site can be increased by, for example, a heating pad, high-intensity focused ultrasound, focused light (e.g., from a laser), or fiber optic techniques known to those having skill in the art. Tracking of the drug loaded P•G NPs may be carried out by imaging for the NP.

In an example, a composition comprises one or more types of P•G NPs of the present disclosure. The drug loaded P•G NPs of the present disclosure may be formulated with conventional pharmaceutical carriers. In an example, a composition comprises one or more types of drug loaded P•G NPs of the present disclosure and one or more carriers. Examples of suitable carriers for administration include water, saline solution, buffer solutions such as phosphate buffers, glycine solutions and the like. Suitable carriers for in vitro use include all of the above and standard culturing media (such as DMEM, α-DMEM, with or without serum such as fetal bovine serum).

Suitable carriers can also include, for example, diluents, adjuvants, excipients, or other vehicles with which the present complexes may be administered to an individual. The formulations may be in an injectable form (for administration via any of the standard injectable routes) to an individual. The individual may be a human being or a non-human animal. Some examples of materials which can serve as pharmaceutical carriers include: sugars, such as lactose, glucose and sucrose; starches, such as corn starch and potato starch; cellulose, including sodium carboxymethyl cellulose, ethyl cellulose and cellulose acetate; powdered tragacanth; malt; gelatin; talc; excipients, such as cocoa butter; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The composition, if desired, can also contain minor amounts of wetting or emulsifying agents, or pH buffering agents. Some examples of compositions suitable for mixing with the agent can be found in: Remington: The Science and Practice of Pharmacy (2005) 21st Edition, Philadelphia, Pa. Lippincott Williams & Wilkins. In one embodiment, the agent is substantially purified (e.g., substantially free from substances that limit its effect or produce undesired side-effects). The formulations may also be made for other delivery routes including via mucosal, muscular, oral, transdermal and the like.

Applications of this invention include but are not limited to drug delivery and/or imaging. The applications of this technology are wide ranging. For example, the promiscuity of the C domain towards hydrophobic drug molecules provides a wide breadth of diseases to treat. The integrin binding domain (RGD) may be substituted for targeting other disease-state biomarkers. In this sense, one can use the cargo loaded polymer-gold nanoparticle nanocomposites as a platform drug delivery vehicle for targeted drug release and/or imaging agents.

The present polymer carriers are drug delivery vehicles that can: a) actively target tumor types; b) exhibit triggered release of a drug at the tumor site; and/or c) possesses the ability to be anatomically imaged for confirmation of vehicle localization at or near the tumor. Use of these delivery vehicles can potentially limit off-target effects of therapeutic agents (such as doxorubicin) and maximize their delivery to the desired site (such as a tumor).

In this disclosure, we provide illustrative examples using two diblocks $E_1C\text{-}His_6$ and $CE_1\text{-}His_6$ each bearing an N-terminal hexahistidine tag for the templated-synthesis of P•G NPs in situ to yield the nanocomposites $E_1C\text{-}His_6$•GNP and $CE_1\text{-}His_6$•GNP, respectively (FIG. 1). These protein polymers have desirable thermostability and superior small molecule binding abilities. $E_1C\text{-}His_6$•GNP and $CE_1\text{-}His_6$•GNP demonstrate elevated inverse temperature transitions, improved small molecule loading capacity, sustained release and enhanced uptake by cancer cells when compared to protein polymers alone.

The steps of the methods described in the various embodiments and examples disclosed herein are sufficient to produce the hybrid materials of the present disclosure. Thus, in an embodiment, a method consists essentially of a combination of the steps of the methods disclosed herein. In another embodiment, the method consists of such steps.

The following examples are presented to illustrate the present disclosure. They are not intended to be limiting in any manner.

EXAMPLE

Figure 2:
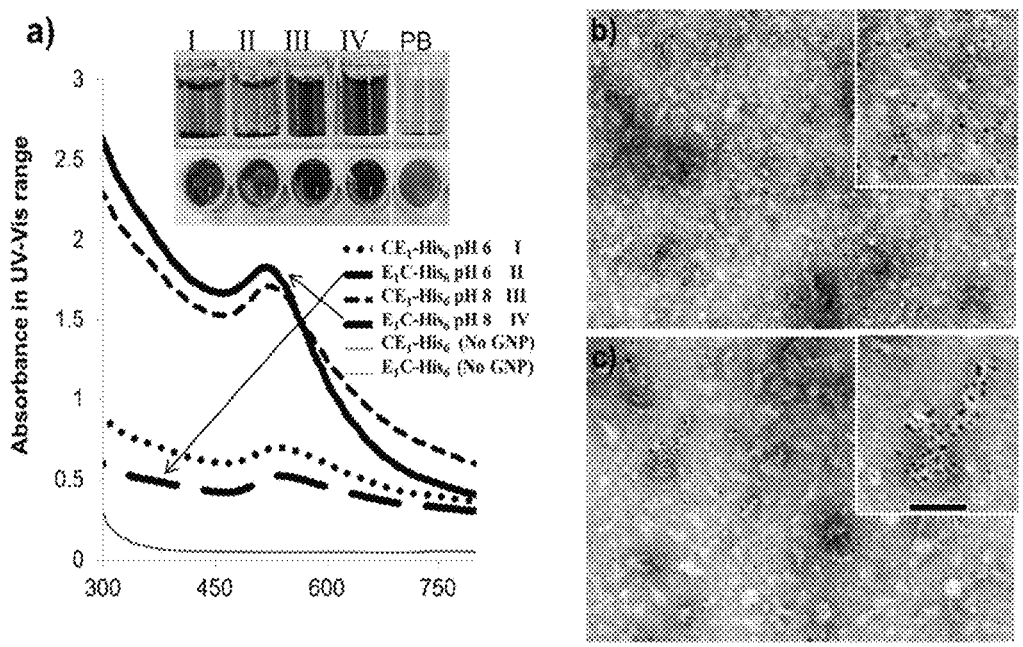
FIG. 2 shows in situ P•G NP templated-synthesis by protein polymer sequences. (a) UV-Vis spectra of P•G NPs at pH 6 and pH 8 (inset shows the templated-synthesis products of $CE_1$-$His_6$•GNP pH 6 (I), $E_1C$-$His_6$•GNP pH 6 (II), $CE_1$-$His_6$•GNP pH 8 (III), $E_1C$-$His_6$•GNP pH 8 (IV) and phosphate buffer•GNP pH 8 (PB)). TEM images of (b) $CE_1$-$His_6$•GNP and (c) $E_1C$-$His_6$•GNP at pH 8.
Figure 3:
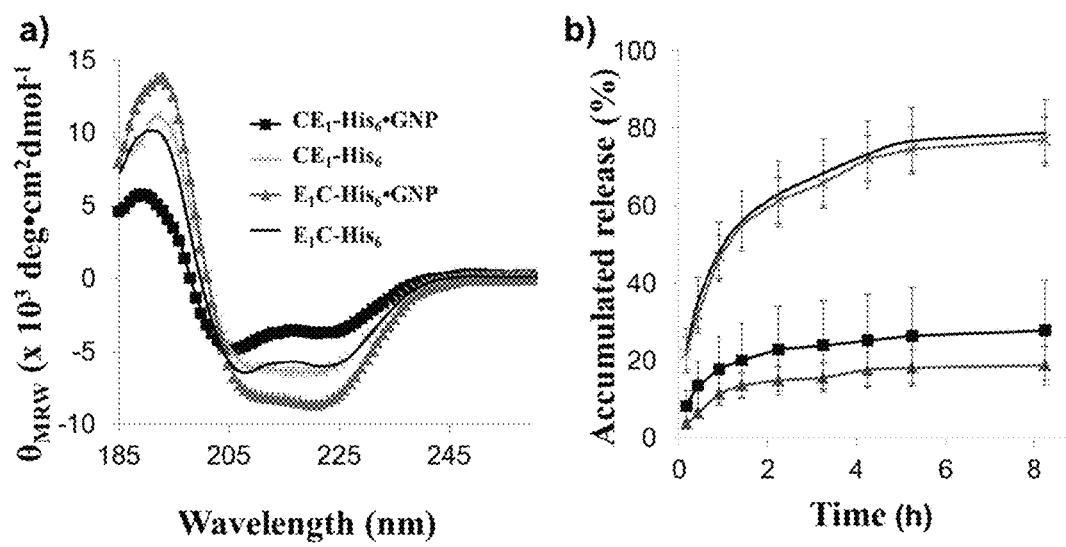
FIG. 3 shows (a) Circular dichroism (CD) wavelength scans of protein polymers in the absence and presence of GNP. (b) Accumulated release of curcumin as a function of time.

This example describes the production of stable P•G NPs by GNP templated-synthesis through engineered N-terminal hexahistidine sequences within the protein diblocks $CE_1\text{-}His_6$ and $E_1C\text{-}His_6$. Either removing the hexahistidine sequence or decreasing the pH to alter the protonation state of the histidine residues does not lead to significant P•G NP production (FIG. 2). After confirming GNP templated-synthesis to $CE_1\text{-}His_6$ and $E_1C\text{-}His_6$ spectroscopically, secondary structure analysis reveals that although a slight loss in alpha helicity is observed, the nanocomposites maintain overall conformation (FIG. 3a). While in situ P•G NP templated-synthesis does not dramatically alter the protein polymer conformations, it impacts their thermoresponsive behavior. The marked effects on the thermoresponsiveness upon P•G NP templated-synthesis by the $CE_1\text{-}His_6$ and $E_1C\text{-}His_6$ protein polymers, regardless of the orientation of the domains can explain the improved loading capacity for curcumin. Upon P•G NP templated-synthesis, the nanocomposites possessed elevated inverse temperature transitions (Table 1), indicative of heightened resistance to coacervative temperature-induced conformation changes. The enhanced stability against coacervation could impose greater mobility via increased hydration on the P•G NPs thereby exposing more non-specific sites for curcumin binding leading to improved loading capacity.

Materials and Methods
General

Yeast extract and curcumin were obtained from Acros Organics (Geel, Belgium). Tryptic soy agar and gold(III) chloride trihydrate were acquired from MP Biomedicals (Santa Ana, Calif.). Ampicillin, isopropyl β-D-1-thiogalactopyranoside (IPTG), imidazole, sodium monobasic phosphate, sodium dibasic phosphate, sodium dodecyl sulfate, sodium hydroxide, sodium chloride, sucrose, tris-hydrochloride, tryptone, PFU high fidelity, DpnI, ACS grade methanol and urea were obtained from Fisher Scientific (Pittsburgh, Pa.). 4-(2-hydroxyethyl)-1-piperazineethanesulfonic acid (HEPES), magnesium sulfate, nickel chloride, sodium borohydride were purchased from Sigma Aldrich (St. Louis, Mo.). Tricine was purchased from Alfa Aesar (Ward Hill, Mass.). Glacial acetic acid and Factor Xa cleavage kit were purchased from EMD Millipore (Rockland, Mass.). Ethyl acetate was purchased from Pharmco-AAPER (Brookfield, Conn.). Ethylenediaminetetraacetic acid (EDTA) and hydrochloric acid were acquired from VWR (Radnor, Pa.). HPLC grade methanol was obtained from Ricca Chemical Company (Arlington, Tex.). Sephadex™ G-25 medium beads were purchased from Amersham Pharmacia Biotech AB (Piscataway, N.J.). Columns were purchased from Bio-Rad (Hercules, Calif.).

Site-Directed Mutagenesis pQE30/$CE_1$ and pQE30/$E_1C$ were employed for production of $CE_1\text{-}His_6$ and $E_1C\text{-}His_6$ proteins in this study (Dai et al., *Biomacromolecules* 2011, 12, (12), 4240-4246). In order to generate proteins with Factor Xa IEGR cleavage site, site-directed mutagenesis was performed using the following primers: 5'-cgcagtagcagcgagctcgcgcccttctatgtgatggtgatggtg-3' (SEQ ID NO: 31) and 5'-cgcgctagccgcaatgcgcccttctatgtgatggtgatggtg-3' (SEQ ID NO: 32) and their reverse complements to generate pQE30/$CE_1$-IGER and pQE30/$E_1C$-IGER respectively. Following the standard protocol for parent strand digestion using Dpn1 the resulting product was transformed into XL1-Blue cells for future use. Mutations were verified by DNA sequencing at Eurofins (Huntsville, Ala.).

Protein Expression and Purification

Figure 7:
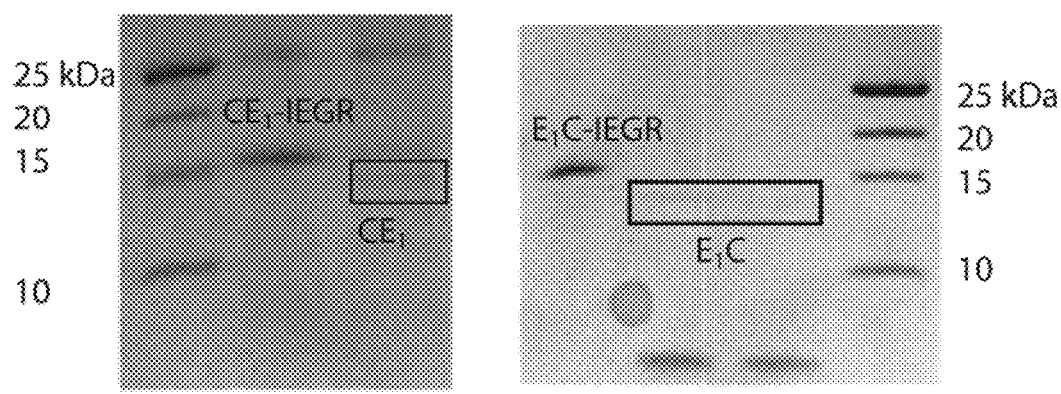
FIG. 7 shows 12% SDS-PAGE verified cleavage of $CE_1$-IEGR and $E_1C$-IEGR on IEGR (SEQ ID NO: 17) site by Factor Xa. Molecular weight of $CE_1$-IEGR and $E_1C$-IEGR are 14150.95 and 13950.75 Da respectively. After His tag and IEGR (SEQ ID NO: 17) site removal, molecular weight of $CE_1$ and $E_1C$ are 12441.08 and 12240.88 Da respectively.

Biosynthesis and purification of $CE_1\text{-}His_6$, $E_1C\text{-}His_6$, $CE_1$-IEGR and $E_1C$-IEGR, was performed (FIG. 6). PQE30/$CE_1$, PQE30/$E_1C$, PQE30/$CE_1$-IGER and PQE30/$E_1C$-IGER were used to express the $CE_1\text{-}His_6$, $E_1C\text{-}His_6$, $CE_1$-IEGR and $E_1C$-IEGR proteins, respectively. All proteins were purified on a HiTrap IMAC FF column charged with nickel under denaturing conditions. For the negative control, $CE_1$-IEGR and $E_1C$-IEGR were dialyzed in 10 mM sodium phosphate buffer, pH 8.0, using SnakeSkin dialysis tubing (Thermo Scientific, 3.5 K MWCO). Factor Xa cleaves the protein after IEGR (SEQ ID NO: 17) site, removing the His-tag. This reaction occurs in 1 μL of 0.5 unit/μL enzyme, 44 μL protein sample of 0.2 mg/mL concentration and 5 μL cleavage buffer (final cleavage buffer condition is 2 mM Tris-HCl, 50 mM NaCl, 0.5 mM $CaCl_2$, pH 7.25). This ratio was scaled up to cleave 4 mL of the samples and cleavage reaction was allowed for 4 days at 4° C. This solution containing cleaved protein, His-tag and Factor Xa was transferred into Factor Xa capture resin and then passed through nickel beads to isolate the cleaved $CE_1$ and $E_1C$ (FIG. 7). After confirming the purity using sodium dodecyl sulfate-polyacrylamide gel electrophoresis (SDS-PAGE), $CE_1\text{-}His_6$, $E_1C\text{-}His_6$, $CE_1$ and $E_1C$ were dialyzed into 10 mM sodium phosphate buffer, pH 8.0. The concentrations of all proteins were determined by a micro BCA assay.

Gold Nanoparticle Templated-Synthesis

A 0.1 M $HAuCl_4 \cdot 3H_2O$ solution (reactive gold solution) was prepared in $dH_2O$. Approximately, 1.2 μL of the reactive gold solution was added into 300 μL of 10 μM protein sample, followed by gentle vortex for 10 minutes at room temperature. To the mixture, a 3.6 μL freshly prepared 0.1 M $NaBH_4$ solution in $dH_2O$, was added to reduce $Au^{3+}$ to $Au^0$. The mixture was then gently rotated to prevent aggregation or uneven templated-synthesis. The reaction was carried at room temperature for 1 hour. The molar ratio of Au' to protein was 40 to 1, while the $NaBH_4$ to $Au^{3+}$ ratio was 2.5 to 1. The resulting protein polymer•gold nanoparticle (P•GNP) nanocomposites were stored at room temperature for 1 hour before further characterization.

Absorbance Spectroscopy

The absorbance spectrum from 200 nm-1000 nm of each P•G NP was scanned using SpectraMax M2 (Molecular Devices) in UV-transparent 96 well microplate (Corning, half area flat bottom). As a control, buffer, $CE_1$-$His_6$ and $E_1C$-$His_6$, in addition to the cleaved $CE_1$ and $E_1C$ proteins at pH 8 were scanned. All protein samples were prepared at 10 µM in 10 mM sodium phosphate buffer, pH 8.0.

Transmission Electron Microscopy

Transmission electron microscopy (TEM) was used to identify the nanometer-sized structures that resulted from self-assembly at room temperature. Samples were prepared in water at 10 µM concentrations in 10 mM sodium phosphate buffer pH 8.0. The samples were gently mixed and applied on a carbon coated 400 mesh Cu/Rh grids and negatively stained with 1% uranyl acetate. The images of the samples were collected on a Phillips CM12 TEM instrument at 120 kV. The particle area and size were measured using ImageJ. The protein particle sizes were determined from at least >130 particles, while sizes of the resulting P•G NPs were determined from at least >130 particles via ImageJ. A histogram of the P•G NP sizes was generated to determine the average size distribution.

Circular Dichroism (CD) Spectroscopy

Wavelength-dependent circular dichroism (CD) spectra were collected on a Jasco J-815 CD Spectrometer equipped with a PTC-423 S single position Peltier temperature control system and counter-cooled with an Isotemp 3016S (Fisher Scientific) water bath. Samples were loaded in a Hellma 218 quartz cuvette (500 µL, 1 mm path length). A far-UV temperature-dependent wavelength scan from 185-260 nm as a function of temperature was completed for $CE_1$-$His_6$ and $E_1C$-$His_6$ in the absence and presence of GNPs at 0.2 mg/mL in 10 mM sodium phosphate buffer pH 8.0 at scan rate of 50 nm/min for a range of temperatures (25-90° C.) with 3 accumulation scans. At least two batches of separately purified proteins were measured. CD data was converted into mean residue molar ellipticity (MRW) via equation $[\theta]_{MRW}=\theta \cdot MW/(10 \cdot n \cdot C \cdot l)$, where $\theta$ is in mdeg, MW is molecular weight, n is amino acid number in protein, C is concentration in mg/mL, l is path length in cm. Fitting and calculation of protein secondary structure was processed with CDSSTR methods. Parameters for the calculation using CDSSTR program were identical to Dai et al. (*Biomacromolecules* 2011, 12, (12), 4240-4246).

Turbidometry

The turbidometry, or inverse temperature transition ($T_t$), was determined via UV-Vis Spectrophotometer Cary-50 (Agilent Technology) equipped with TC 125 temperature controller (Quantum Northwest) in Type 21 quartz cuvette with 10 mm path length (Buck Science) by monitoring the change in turbidity at 800 nm from 25° C. to 80° C. at a rate of 1° C./min. Protein stock solutions for $T_t$ measurement were prepared in 0.2 mg/mL (or 14.3 µM and 14.4 µM for $CE_1$-$His_6$ and $E_1C$-$His_6$, respectively) in 10 mM sodium phosphate buffer, pH 8.0. In order to bring $T_t$ value of all the samples into instrument operation range, highly concentrated NaCl solution was added prior to $T_t$ measurement (Table 1). Measurements were performed on at least two different protein sample preps to calculate the average $T_t$. The $T_t$ was determined at the midpoint of the normalized turbidity.

TABLE 1

Final concentration of protein and NaCl in samples for $T_t$ measurement

|  | $CE_1$-$His_6$ | $CE_1$-$His_6$•GNP | $E_1C$-$His_6$ | $E_1C$-$His_6$•GNP |
|---|---|---|---|---|
| Concentration of protein | 0.1621 mg/mL | 0.1621 mg/mL | 0.1818 mg/mL | 0.1818 mg/mL |
| Concentration of NaCl | 0.946M | 0.946M | 0.45M | 0.45M |

Small Molecule Loading and Release

Curcumin (6.5 nmol final concentration from 3 mM stock solution in HPLC grade methanol) was incubated with 1.3 nmol of $CE_1$-$His_6$, $E_1C$-$His_6$, $CE_1$-$His_6$•GNP and $E_1C$-$His_6$•GNP at room temperature for 2 hours and loaded onto Bio-Rad Spin6 columns packed with Sephadex G-25 medium beads 0.5 cm high. Bound protein polymer•curcumin complexes (in the presence or absence of GNP) were eluted by size, washed 3 times in 50 µL sodium phosphate buffer, followed by centrifugation for 5 min at 14000 rpm. The beads containing unbound curcumin were collected separately and resuspended back to buffer for solvent extraction. Both bound and unbound curcumin were extracted by adding 150 µL ethyl acetate and quantitatively determined by measuring absorbance at 416 nm. Absorbance was measured in a Hellma 105.201-QS type cuvette (10 mm light path, 100 µL sample) on SpectraMax M2. This binding study was performed on at least three different protein sample preparations to calculate the average loading capacities with errors represented as the standard deviation of the three trials.

Release of curcumin from $CE_1$-$His_6$, $E_1C$-$His_6$, $CE_1$-$His_6$•GNP and $E_1C$-$His_6$•GNP was then investigated. Curcumin (26 nmol) was added to 200 µL of 26 µM (5.2 nmol) protein sample. After 2 hours of incubation at room temperature, the solution was adjusted to contain a final concentration of 0.5 M NaCl. The protein polymer•curcumin complex (in the presence or absence of GNP) were incubated at 45° C. (well above the TO for 30 min and centrifuged to separate protein polymer•curcumin complex from excess curcumin. The pellets were resuspended in 200 µL of 50 mM phosphate buffer, pH 7.4 and kept at room temperature in the dark for release. After 10 min, the suspensions were centrifuged and the supernatant was removed and used for extraction assessment of released curcumin. This resuspension-incubation-spin-release cycle was repeated for the next eight hours at the following time points: 10, 25, 55, 85, 135, 195, 255, 315 and 495 min. Release study was performed on two different protein sample preparations to obtain the averaged release profile. Error bars on the release data represented standard error of the two sample preparations.

Cell Culture Studies

MCF7 human breast cancer cells were obtained from ATCC and maintained at 37° C., 5% $CO_2$ as monolayer cultures in Dulbecco's modified Eagle's medium (DMEM with high glucose containing phenol red) supplemented with 10% (v/v) fetal bovine serum (FBS), gentamicin (50 µg/mL), 100 U penicillin/100 µg/mL streptomycin. Because the loading capacities of curcumin for P•GNP nanocomposites are much larger than those of the proteins in the absence of GNP we prepared two corresponding curcumin controls that represented the bound curcumin levels in P•G NPs and protein polymers alone (Table 2). To avoid any uptake of unbound curcumin by the cells directly, we limited the curcumin amount that is equivalent to the loading capacity of 26 µM of protein samples in 50 mM sodium phosphate buffer, pH 7.4 and allowed to bind for 2 hours at room temperature prior to cell culture studies.

TABLE 2

Final concentration (μM) of each component in samples for cell uptake experiment.

|  | $CE_1$-$His_6$ | $CE_1$-$His_6$•GNP | $CE_1$-$His_6$-CCM1[a] | $CE_1$-$His_6$•GNP-CCM2[a] | CCM2[b] |
|---|---|---|---|---|---|
| Conc. of protein | 10 | 10 | 10 | 10 | N/A |
| Conc. of CCM | N/A | N/A | 4.27 | 46.32 | 46.32 |

|  | $E_1C$-$His_6$ | $E_1C$-$His_6$•GNP | $E_1C$-$His_6$-CCM3[a] | $E_1C$-$His_6$•GNP-CCM4[a] | CCM4[b] |
|---|---|---|---|---|---|
| Conc. of protein | 10 | 10 | 10 | 10 | N/A |
| Conc. of CCM | N/A | N/A | 1.58 | 40.10 | 40.10 |

[a]CCM added in uptake experiment are equivalent to the loading capacities of each protein sample
[b]For CCM controls, the amount equivalent to P•GNP loading capacities was used Multiple sets of experiments were performed to record curcumin uptake by image acquisition using FITC filter (Em: 520 nm) under fluorescence microscopy and direct measurement of curcumin uptake in cell extractions. Cells were grown directly on 24-well culture plates ($8 \times 10^4$ cells/well) for cell extraction or on cover slips for microscopy. After 24 hours of cell plating, cells were treated for 4 or 24 hours with different combination of proteins with or without GNP and/or curcumin. For all the treatments, the total volume of samples with DMEM in 24-well plates was kept constant at 300 μL with proteins prepared at 10 μM concentrations. The ratio of sample amount to number of cells was also kept constant. The results are representative of two such independent sets of experiments.

For direct measurement of curcumin uptake, cells were washed with Dulbecco's phosphate buffered saline and lysed with 200 μL RIPA/well (25 mM TrisHCl pH7.6, 150 mM NaCl, 1% NP-40, 1% sodium deoxycholate, 0.1% SDS) at room temperature for 20 min with gentle shaking. Lysed cells were then collected and vortexed. For curcumin extraction, 150 μL ethyl acetate was added the lysed cells. Thorough extraction was ensured by violently shaking the lysate-solvent mixture for 30 seconds. Curcumin containing solvent phase was then separated by centrifuging at 14,000 RPM for 2 minutes at room temperature. Absorbance of curcumin in ethyl acetate was measured using SpectraMax M2 (Molecular Devices) in Hellma 105.201-QS type quartz cuvette (100 μL volume, 10 mm light path) at 416 nm.

For fluorescent imaging of curcumin uptake, cells on coverslips were fixed with 300 μL 4% paraformaldehyde solution in DPBS for 20 minutes at room temperature on a plate rocker. Following fixation, cell-containing coverslips were washed 3×300 μL DPBS and were mounted on glass slides using DAPI containing mounting medium (Southern Biotech Dapi Fluoromount-G). Coverslips were then sealed using clear nail polish for viewing under microscopy and long-term storage. Cells were viewed using fluorescence microscope IX71 (Olympus) using DAPI (for cell nuclei) and FITC (for curcumin uptake) at 60× magnification while keeping the exposure time for the FITC images constant at 200 milliseconds.

Cell viability measurements were carried out using a CellTiter 96® Aqueous One solution kit (Promega) in a 96-well plate, seeded $1 \times 10^4$ cells/well. After 24 hours, the cells were treated for 4 hours or 24 hours with protein polymers and P•G NPs with and without curcumin along with control treatments of curcumin alone and media alone. After the treatment periods, 20 μL [3-(4,5-dimethylthiazol-2-yl)-5-(3-carboxymethoxyphenyl)-2-(4-sulfophenyl)-2H-tetrazolium (MTS) was added to each well, followed by incubation at 37° C. for 3 hours. The plate was centrifuged for 3 minutes at 2500 rpm and then subjected to absorbance measurements at 490 nm (Tables 3 and 4).

TABLE 3

MTS Assay after 4 Hour Treatment

|  | $CE_1$-$His_6$ | $CE_1$-$His_6$•GNP | $CE_1$-$His_6$-CCM1 | $CE_1$-$His_6$•GNP-CCM2 | CCM1 | CCM2 | Cell only |
|---|---|---|---|---|---|---|---|
| Abs. | 2.07 ± 0.01 | 2.028 ± 0.01 | 2.046 ± 0.01 | 2.046 ± 0.01 | 1.999 ± 0.05 | 2.025 ± 0.02 | 2.045 ± 0.01 |

|  | $E_1C$-$His_6$ | $E_1C$-$His_6$•GNP | $E_1C$-$His_6$-CCM1 | $E_1C$-$His_6$•GNP-CCM2 | CCM1 | CCM2 | DMEM |
|---|---|---|---|---|---|---|---|
| Abs. | 2.053 ± 0.00 | 2.042 ± 0.02 | 2.034 ± 0.02 | 2.042 ± 0.01 | 2.039 ± 0.00 | 2.044 ± 0.01 | 0.00 ± 0.00 |

TABLE 4

MTS Assay after 24 Hour Treatment

|  | $CE_1$-$His_6$ | $CE_1$-$His_6$•GNP | $CE_1$-$His_6$-CCM1 | $CE_1$-$His_6$•GNP-CCM2 | CCM1 | CCM2 | Cell only |
|---|---|---|---|---|---|---|---|
| Abs. | 2.138 ± 0.01 | 2.051 ± 0.01 | 2.041 ± 0.00 | 2.026 ± 0.03 | 2.034 ± 0.02 | 1.999 ± 0.01 | 2.017 ± 0.05 |

|  | $E_1C$-$His_6$ | $E_1C$-$His_6$•GNP | $E_1C$-$His_6$-CCM1 | $E_1C$-$His_6$•GNP-CCM2 | CCM1 | CCM2 | DMEM |
|---|---|---|---|---|---|---|---|
| Abs. | 2.119 ± 0.00 | 1.999 ± 0.02 | 2.034 ± 0.00 | 1.866 ± 0.15 | 1.974 ± 0.01 | 1.98 ± 0.04 | 0.00 ± 0.00 |

Results

Fabrication of P•G NPs

Figure 8:
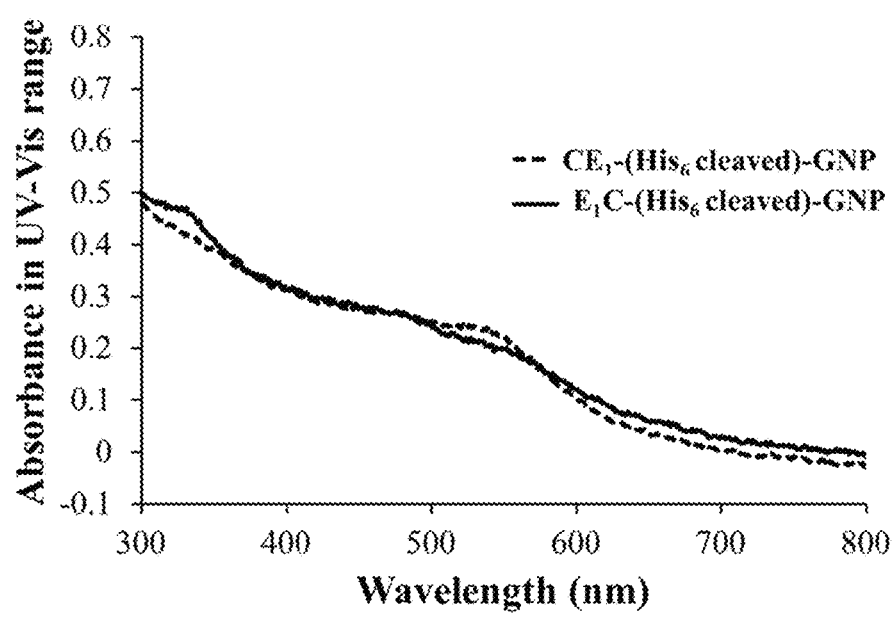
FIG. 8 shows UV-Vis spectra of $CE_1$-($His_6$ cleaved)-GNP and $E_1C$-($His_6$ cleaved)-GNP. The spectra for phosphate buffer supplemented with Factor XA cleavage buffer and GNP was subtracted from each spectra.

Both $CE_1$-$His_6$ and $E_1C$-$His_6$ were biosynthesized through recombinant bacterial expression and purified via nickel affinity resin. The protein diblock polymers were subject to P•G NP templated-synthesis without use of capping reagents. Gold salt ($HAuCl_4$) solution was directly added to protein samples, followed by reduction with $NaBH_4$ under pH 6 and 8 (FIG. 2a). Surprisingly, the P•G NPs were stable at pH 8; within one week, absorbance spectra of complexes remained nearly the same with no observed precipitation even after one month when stored at room temperature. The $CE_1$-$His_6$•GNP and $E_1C$-$His_6$•GNP exhibited successful templated-synthesis of P•G NPs with a distinct red-brown color change, confirmed by an observable peak at ~520 nm under pH 8 (FIG. 2a). Since the lone pair electron on $\epsilon^2N$ of histidine is protonated at pH≤6, the protein polymer did not undergo P•G NP templated-synthesis very well under pH 6 conditions. Both $CE_1$-$His_6$ and $E_1C$-$His_6$ in the absence of gold salt did not lead to any detectable absorption peak at 520 nm (FIG. 8); gold salt (PB, pH 8) in the absence of protein did not produce signal indicating that the protein polymers were necessary for P•G NP templated-synthesis (FIG. 2a). To affirm that the P•G NP templated-synthesis was due to the $His_6$ tag, proteins lacking the N-terminal $His_6$ sequence did not exhibit a strong signal at 520 nm (FIG. 8).

Morphological Characterization of P•G NPs

Figure 9:
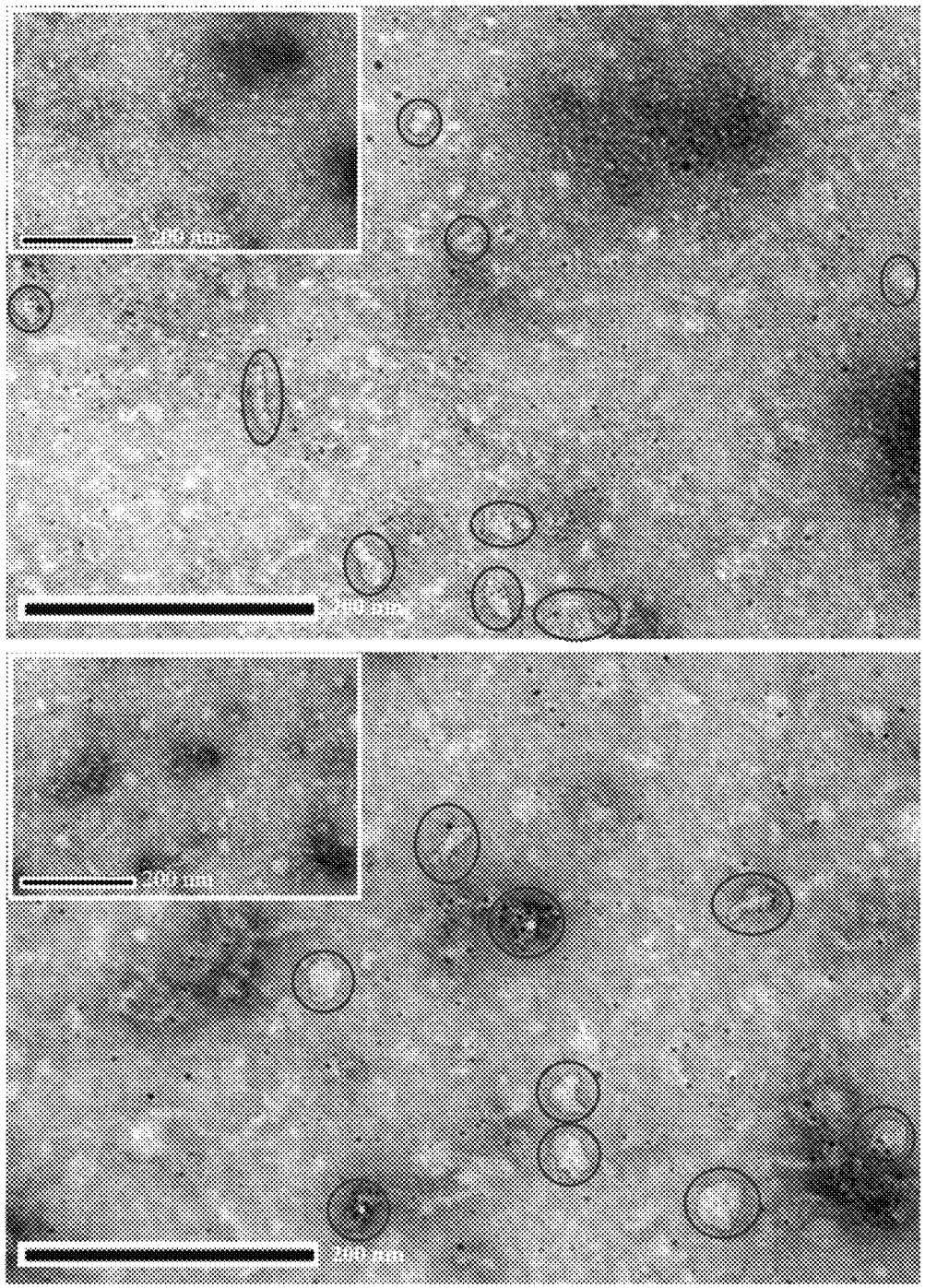
FIG. 9 shows protein size measurements. Micrographs of $CE_1$-$His_6$•GNP (top) and $E_1C$-$His_6$•GNP (bottom) with protein particles highlighted (with black circle). Selected protein particles are analyzed for size measurements using ImageJ.
Figure 10:
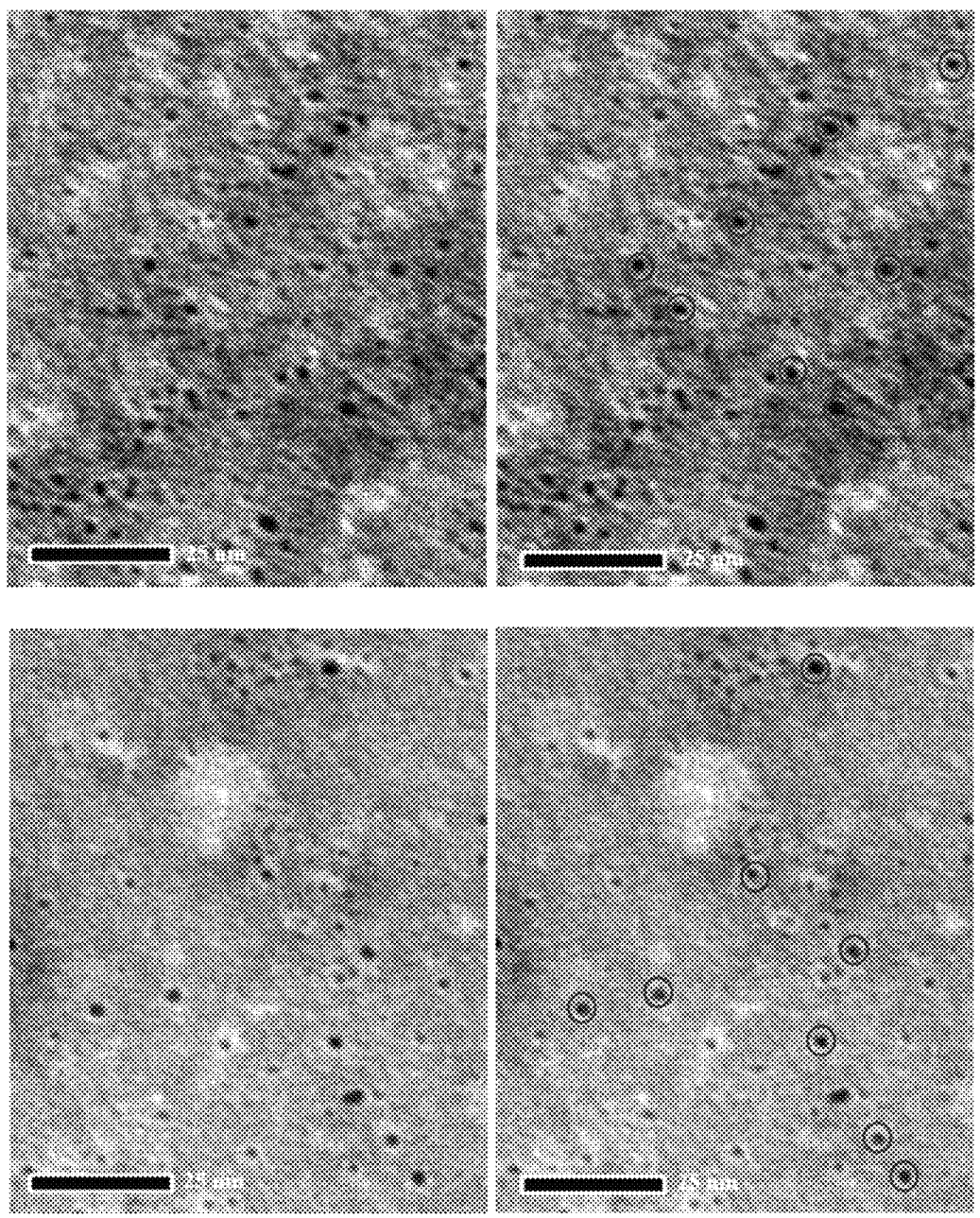
FIG. 10 shows micrographs of $CE_1$-$His_6$•GNP (upper panel) and $E_1C$-$His_6$•GNP (lower panel) samples with selected GNPs (with black circle, right side) for size measurements using ImageJ.
Figure 11:
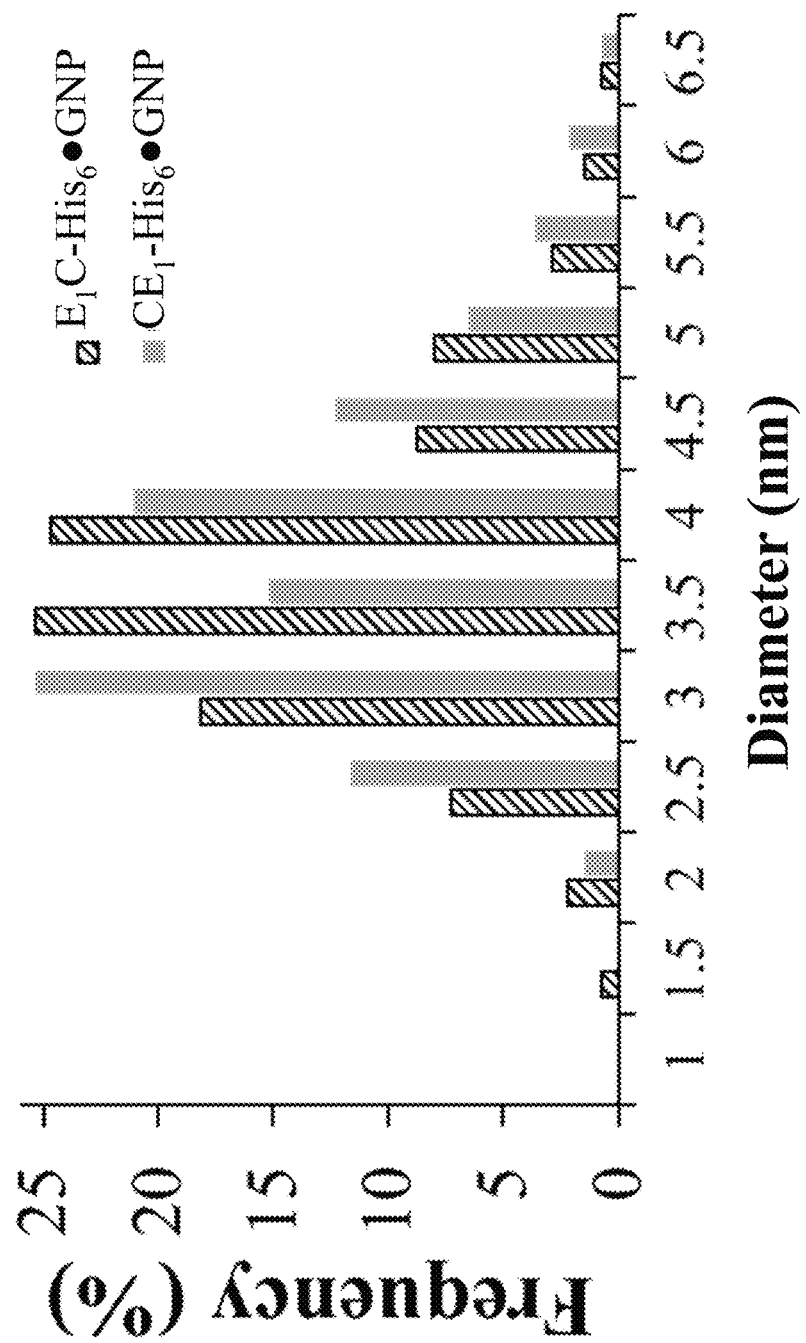
FIG. 11 shows the size distribution of GNPs in each protein construct. More than 130 particles were analyzed for both constructs. The average diameter of GNPs in $E_1C$-$His_6$•GNP is 3.5±0.9 nm and 3.4±0.9 nm in $CE_1$-$His_6$•GNP.

To assess the morphology and sizes of the P•G NPs, transmission electron microscopy (TEM) was performed (FIG. 2b, c). The $CE_1$-$His_6$•GNP and $E_1C$-$His_6$•GNP assembled into nanoparticles with diameters of 23.8±5.6 nm and 23.9±5.2 nm, respectively (Table 5, FIG. 9). Average diameters of GNPs in both $CE_1$-$His_6$•GNP and $E_1C$-$His_6$•GNP were 3.4±0.9 nm and 3.5±0.9 nm, respectively (Table 5, FIG. 10). The observed absorption peak at 520 nm is due to the GNP diameters being within 2-10 nm range (FIG. 11).

Secondary Structure Analysis of P•G NPs

Figure 12:
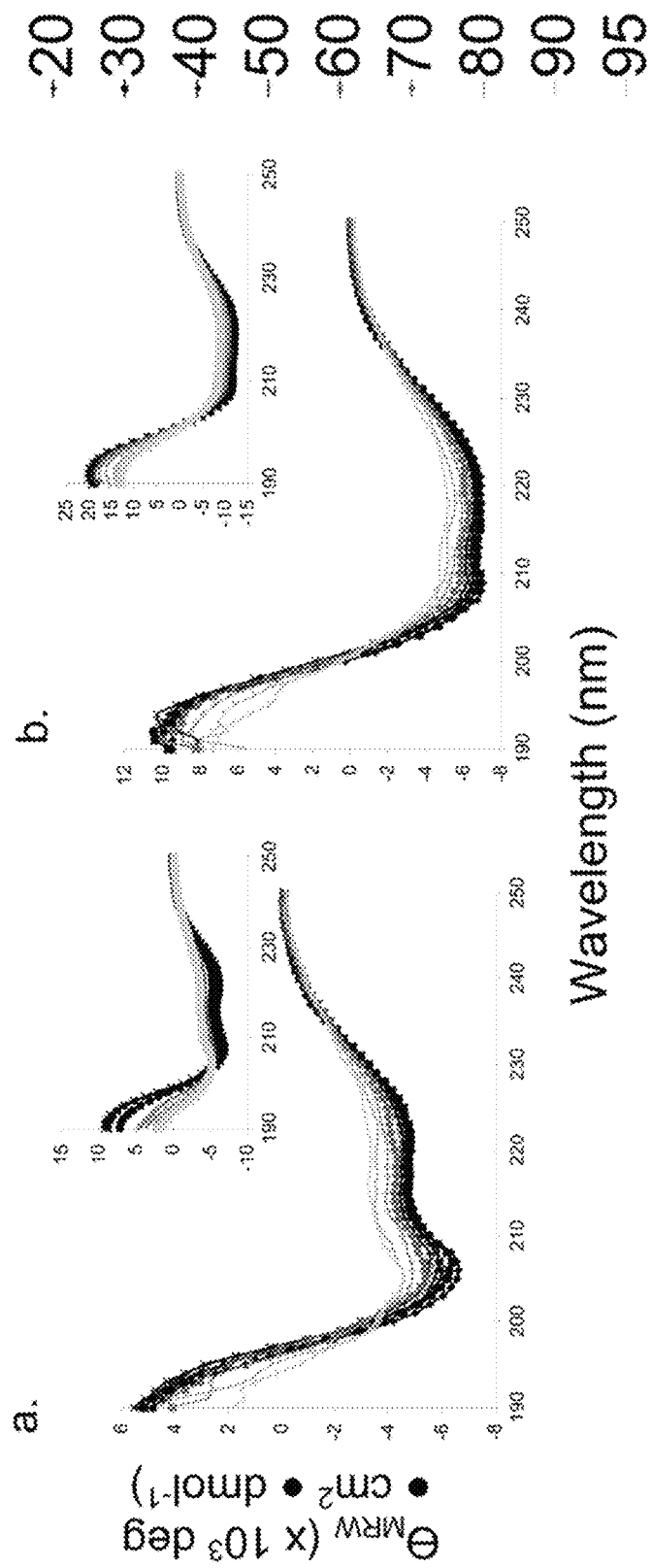
FIG. 12 shows temperature dependent CD wavelength scans of (a) $CE_1$-$His_6$•GNP and (b) $E_1C$-$His_6$•GNP from 20° C. to 95° C. Insets represent the temperature-dependent CD wavelength scans of the same protein in the absence of GNP templated-synthesis.
Figure 13:
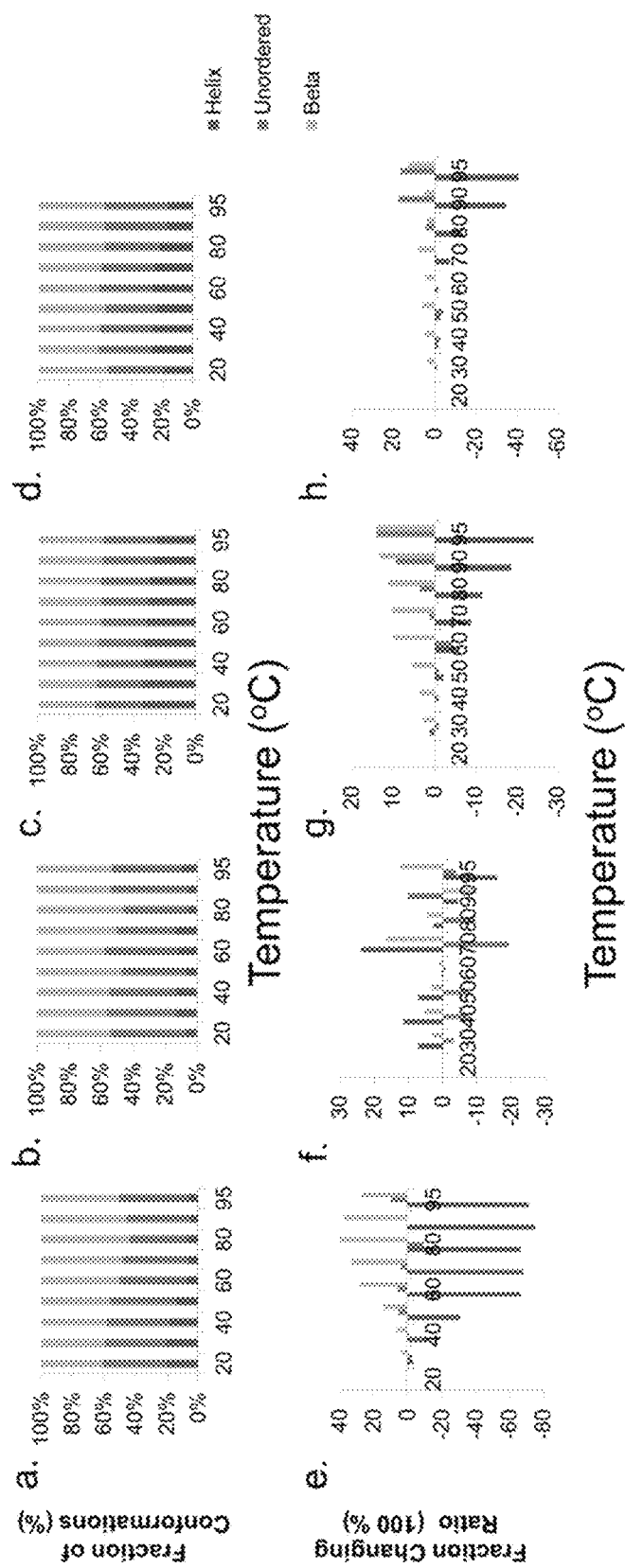
FIG. 13 shows the secondary structure calculation using CDSSTR of (a) $CE_1$-$His_6$, (b) $CE_1$-$His_6$•GNP, (c) $E_1C$-$His_6$ and (d) $E_1C$-$His_6$•GNP at pH 8.0. The change in fraction of secondary structure as a function of temperature for (e) $CE_1$-$His_6$, (f) $CE_1$-$His_6$•GNP, (g) $E_1C$-$His_6$ and (h) $E_1C$-$His_6$•GNP via CDSSTR.

A comparison of the secondary structures in the presence and absence of GNP was performed via circular dichroism (CD) to determine whether P•G NP templated-synthesis affected the protein polymer conformations (FIG. 3a). While the overall shape of the wavelength scans were maintained, a slight loss in structure was observed for $CE_1$-$His_6$•GNP and $E_1C$-$His_6$•GNP relative to $CE_1$-$His_6$ and $E_1C$-$His_6$, respectively (FIGS. 3a, 12, and 13). To assess the impact of P•G NP templated-synthesis on the inverse temperature transition ($T_t$), the UV/vis absorbance of $CE_1$-$His_6$•GNP and $E_1C$-$His_6$GNP at 800 nm was monitored as a function of temperature (Table 5). Relative to the parent protein polymers, $CE_1$-$His_6$•GNP and $E_1C$-$His_6$•GNP revealed an increase in $T_t$ by 11.2° C. and 8.3° C., respectively.

Curcumin Loading and Release

To evaluate the loading capacity of the protein polymers in the absence and presence of GNP, curcumin was incubated with $CE_1$-$His_6$, $E_1C$-$His_6$, $CE_1$-$His_6$•GNP and $E_1C$-$His_6$•GNP for 2 hours. Unbound curcumin was then separated and quantified to determine the amount of curcumin bound to the protein polymer and P•G NP complexes (Table 5). Surprisingly, $CE_1$-$His_6$•GNP exhibited higher binding capacity than $CE_1$-$His_6$ by 8 fold, while $E_1C$-$His_6$•GNP demonstrated a 7.3 fold improvement over $E_1C$-$His_6$.

Release studies were performed by loading the protein polymers and P•G NPs with curcumin and assessing the amount of free curcumin over time. The protein polymers alone released>50% curcumin after 1.4 hrs (hours); both $CE_1$-$His_6$ and $E_1C$-$His_6$ showed rapid and nearly complete release of 77.0% and 78.8% free curcumin by 8.25 hrs (FIG. 3b). By contrast, $CE_1$-$His_6$•GNP and $E_1C$-$His_6$•GNP, revealed a slow and sustained release of 27.9% and 18.8% free curcumin by 8.25 hrs (FIG. 3b). Thus, the P•G NPs s not only increased the binding capacity for curcumin but also, slowed down its release.

Curcumin Uptake by Breast Cancer Cells

Figure 4:
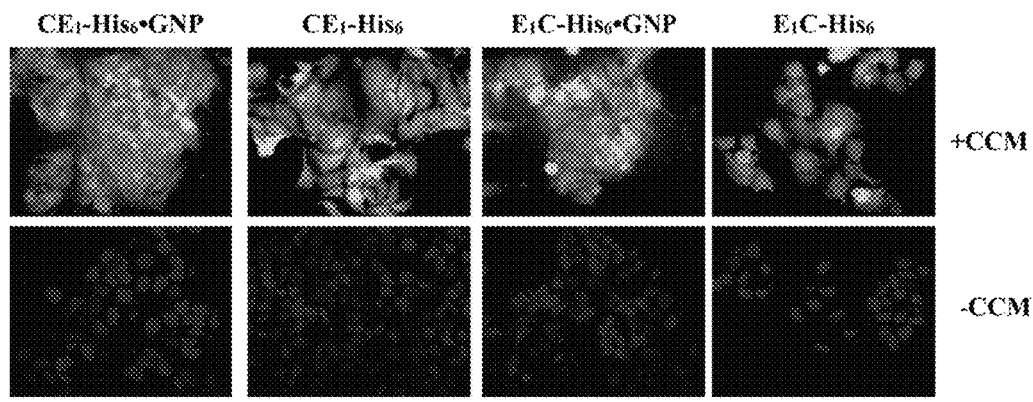
FIG. 4 shows fluorescence microscopy images of MCF-7 cells treated with protein polymers alone or P•G NPs in the absence and presence of curcumin (CCM).
Figure 5:
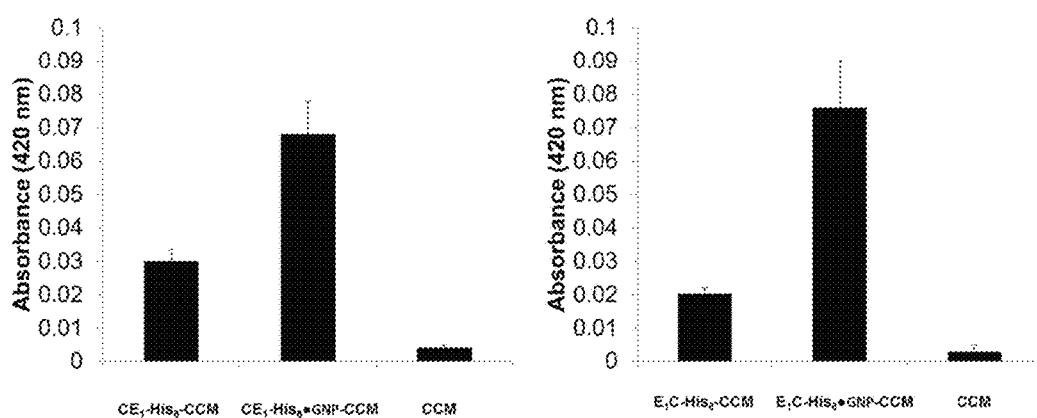
FIG. 5 shows quantification of curcumin uptake in MCF-7 cells via extraction from cells. Absorption plots of (a) $CE_1$-$His_6$-CCM, $CE_1$-$His_6$•GNP-CCM and CCM (p value<0.05) and (b) $E_1C$-$His_6$, $E_1C$-$His_6$•GNP-CCM and CCM (p value<0.05).

As curcumin is insoluble under aqueous conditions and does not effectively penetrate cancer cells alone, we investigated whether the P•G NPs could enhance small molecule delivery and uptake by MCF7 breast cancer cells. Both $CE_1$-$His_6$•GNP and $E_1C$-$His_6$•GNP complexed with curcumin exhibited uptake as visualized by fluorescence (FITC channel); the curcumin appeared to be present in the cytoplasm as demonstrated by the overlay with DAPI stained cells (FIG. 4). We also explored whether the protein polymers alone would deliver curcumin; both $CE_1$-$His_6$ and $E_1C$-$His_6$ revealed uptake albeit substantially less than the P•G NPs (FIG. 4). To assess whether $CE_1$-$His_6$•GNP, $E_1C$-$His_6$•GNP, $CE_1$-$His_6$ and $E_1C$-$His_6$ were themselves toxic to the cells, MTS assays were conducted; neither the protein polymer nor P•G NPs s exhibited cytotoxicity (Tables 3 and 4). Under identical conditions, the curcumin alone control did not show any uptake at the same concentrations of the protein polymers alone and the P•GNP nanocomposites. This was confirmed by quantifying curcumin extracted from the cells. Extraction of curcumin revealed 2.25-fold and 3.75-fold greater amount of available curcumin for $CE_1$-$His_6$•GNP and $E_1C$-$His_6$•GNP, respectively, relative to the protein polymers alone (FIG. 5).

TABLE 5

Particle Sizes, $T_t$ and Loading Capacities of Proteins in the Presence and Absence of GNPs.

| Composite | Size of protein particles (nm) | Size of GNPs (nm) | $T_t$ (° C.) | CCM/P[c] molar binding ratio |
|---|---|---|---|---|
| $CE_1$-$His_6$ | 26.0 ± 3.0[a] | N/A | 55.0 ± 0.8 | 0.40 ± 0.06 |
| $E_1C$-$His_6$ | 27.9 ± 3.7[a] | N/A | 33.8 ± 2.2 | 0.41 ± 0.10 |
| $CE_1$-$His_6$•GNP | 23.8 ± 5.6[b] | 3.4 ± 0.9 | 66.2 ± 0.8 | 3.16 ± 0.44 |
| $E_1C$-$His_6$•GNP | 23.9 ± 5.2[b] | 3.5 ± 0.9 | 42.1 ± 7.1 | 2.95 ± 0.42 |

Figure 14:
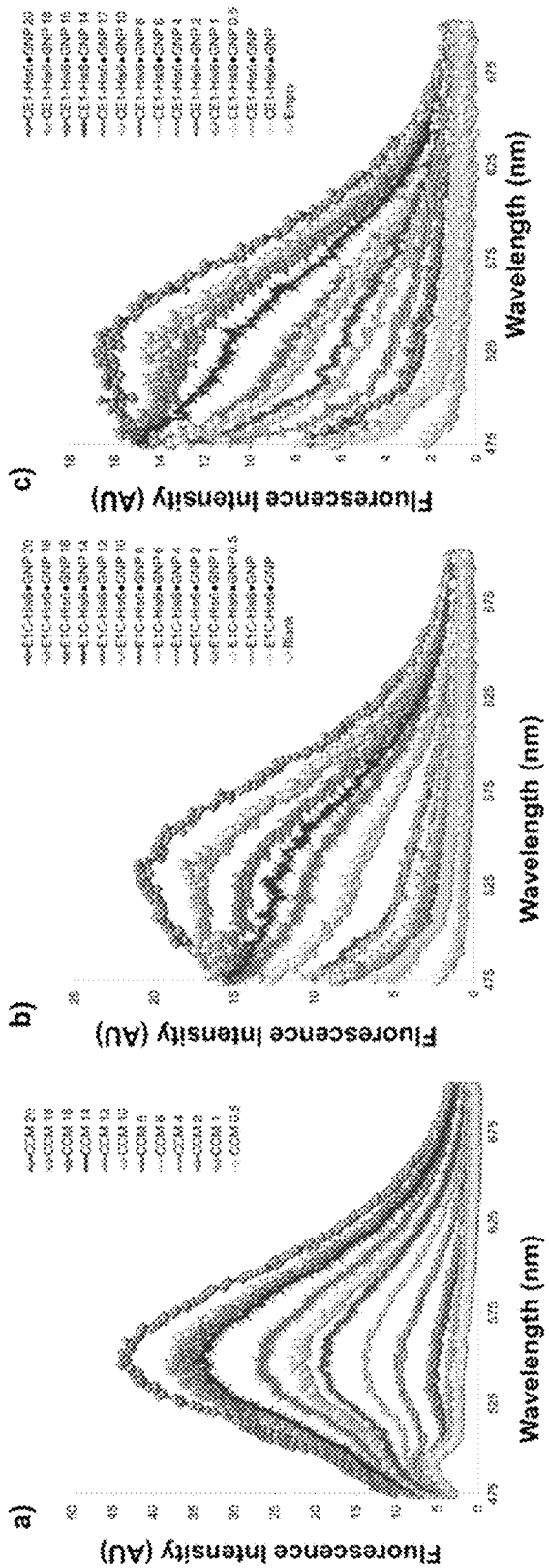
FIG. 14 shows fluorescence, Ex: 420 nm; optical cutoff: 455 nm, of (a) CCM, (b) $E_1C$-$His_6$•GNP and (c) $CE_1$-$His_6$•GNP. Values following each data point represent the micromolar concentration of CCM.

[a]Data from Haghpanah et al., Mol. Biosys. 2010, 6, (9), 1650-1661.
[b]Sizes were measured on P•GNP nanocomposites from >130 particles.
[c]Ratio of Curcumin to protein or P•G NP Small Molecule Binding Properties after Gold Nanoparticle Templated-synthesis and Delivery to Breast Cancer Cells. The C domain present in both diblocks $CE_1$-$His_6$ and $E_1C$-$His_6$ is capable of binding small hydrophobic molecules such as curcumin. This phytochemical possesses medically relevant pharmacological properties yet it fails to remain stable under physiological conditions. Therefore, maximizing curcumin loading capacities and optimizing slower release profiles in carriers would be important for drug delivery. Upon GNP templated-synthesis of both protein diblocks with gold nanoparticles, there is a 7.3 and 8-fold increase in curcumin binding for $CE_1$-$His_6$•GNP and $E_1C$-$His_6$•GNP, respectively, when compared to the protein polymers alone (Table 5). Curcumin is interesting in that it only exhibits fluorescence upon binding to other molecules. The curcumin bound P•G NPs show quenching and a blue shift in the fluorescence spectra suggesting a proximity effect of the GNP on the fluorescence properties of curcumin (FIG. 14). This further affirms that the P•G NPs are binding to the curcumin.

The P•G NPs demonstrate a prolonged release profile whereby nearly 70% of available curcumin was retained within both the P•G NPs after 8.25 hours (FIG. 3b). In contrast, the protein polymers alone released more than 50% of retained curcumin after 1.4 hours. These results translate to successful delivery into MCF-7 cells. Extraction of curcumin from treated MCF-7 cells reveals a greater than 2-fold increase in bioavailable phytochemical by both the nanocomposites relative to their protein polymer counterparts (FIG. 5). The high amount of curcumin recovered from the cells implies chemical protection and half-life extension of the labile, yet biologically active curcumin.

Remarkably, both $CE_1$-$His_6$•GNP and $E_1C$-$His_6$•GNP nanocomposites exhibit improved small molecule loading, slow and extended release as well as effective delivery when exposed to MCF-7 breast cancer cells. These hybrid constructs can greatly broaden the biomaterials candidates for applications in targeted drug delivery. This can be achieved via the incorporation of tumor targeting domains in the solvent exposed residues of the protein polymer. Furthermore, the drug loaded-nanocomposites, by way of templated-synthesis of GNP on the protein polymer, could be used for tandem chemotherapy and light-irradiated phototherapy.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A protein polymer-gold nanoparticle, wherein the gold forms the core of the nanoparticle and a plurality of protein polymer molecules are coordinated to the gold core via a poly-histidine tag present on each protein polymer molecule, wherein the protein polymer molecule comprises one or more elastin-like polypeptide domain (E) and a coiled-coil region of Cartilage Oligomeric Matrix Protein domain (C) or a variant thereof, wherein the variant has at least 70% identity with SEQ ID NO:1.

2. The nanoparticle of claim 1, wherein the average size of the gold core is about 2 to 5 nm.

3. The nanoparticle of claim 1, wherein the average size of the nanoparticle is about 18 to 30 nm.

4. The nanoparticle of claim 2, wherein the average size of the nanoparticle is about 18 to 30 nm.

5. The nanoparticle of claim 1, wherein the protein polymer has the structure $CE_x$-$His_y$ or $E_x$-$His_y$, wherein x is 1-5, and y is 1-10.

6. The nanoparticle of claim 1, wherein the nanoparticle further comprises a small molecule.

7. The nanoparticle of claim 6, wherein the small molecule is a hydrophobic small molecule.

8. The nanoparticle of claim 6, wherein the small molecule is a hydrophilic small molecule.

9. A composition comprising a nanoparticle of claim 1.

10. The composition of claim 9, further comprising a pharmaceutical carrier.

11. A composition comprising protein polymer-gold nanoparticles made by a process comprising:
   a) admixing a composition comprising a gold precursor with a composition comprising a protein polymer, wherein the protein polymer comprises one or more elastin-like polypeptide domain (E) and a coiled-coil region of Cartilage Oligomeric Matrix Protein domain (C) or a variant thereof, wherein the variant has at least 70% identity with SEQ ID NO:1; and
   b) adding a reducing agent to a) for a time sufficient to form the protein polymer-gold nanoparticles.

12. The composition of claim 11, further comprising incubating the protein polymer-gold nanoparticles with a composition comprising hydrophobic small molecules thereby incorporating the small molecules in the protein polymer-gold nanoparticles.

13. A method for delivery of hydrophobic small molecules to a target comprising: administering to an individual a composition comprising protein polymer-gold nanoparticles of claim 1, having incorporated therein hydrophobic small molecules such that the nanoparticles are taken up by target cells and the small molecules are released within the target cells.

14. The method of claim 13, further comprising monitoring the location of the nanoparticles in the individual following administration by magnetic resonance imaging of gold.

15. The method of claim 13, further comprising increasing the temperature of the desired site when the nanoparticles reach the desired site, to a temperature sufficient to facilitate hydrophobic small molecule release from the nanoparticles.

16. The method of claim 15, wherein an increase in the temperature of the desired site is achieved by one or more of the following selected from the group consisting of heating pad, high-intensity focused ultrasound, focused light, and fiber optics.

17. The nanoparticle of claim 1, wherein the variant has at least 75% identity with SEQ ID NO:1.

18. The nanoparticle of claim 1, wherein the variant has at least 80% identity with SEQ ID NO:1.

19. The nanoparticle of claim 1, wherein the variant has at least 85% identity with SEQ ID NO:1.

20. The nanoparticle of claim 1, wherein the variant has at least 90% identity with SEQ ID NO:1.

21. The nanoparticle of claim 1, wherein the variant has at least 95% identity with SEQ ID NO:1.

22. The composition of claim 11, wherein the variant has at least 75% identity with SEQ ID NO:1.

23. The composition of claim 11, wherein the variant has at least 80% identity with SEQ ID NO:1.

24. The composition of claim 11, wherein the variant has at least 85% identity with SEQ ID NO:1.

25. The composition of claim 11, wherein the variant has at least 90% identity with SEQ ID NO:1.

26. The composition of claim 11, wherein the variant has at least 95% identity with SEQ ID NO:1.

* * * * *

UNITED STATES PATENT AND TRADEMARK OFFICE
CERTIFICATE OF CORRECTION

PATENT NO. : 10,463,752 B2
APPLICATION NO. : 15/400342
DATED : November 5, 2019
INVENTOR(S) : Montclare et al.

Page 1 of 1

It is certified that error appears in the above-identified patent and that said Letters Patent is hereby corrected as shown below:

In the Specification

Column 1, Lines 15-18, should read:
--This invention was made with government support under grant nos. DMR1205384, DMR1420073, and DGE0741714 awarded by the National Science Foundation, grant no. CA016087 awarded by the National Institutes of Health, and grant no. W911NF-19-1-0150 awarded by the the United States Army Research Office (ARO). The government has certain rights in the invention.--

In the Claims

Column 33, Line 27, in Claim 5, "$E_x$-$His_y$" should read:
--$E_xC$-$His_y$--

Signed and Sealed this
Second Day of June, 2020

Andrei Iancu
*Director of the United States Patent and Trademark Office*